(12) United States Patent
Keller et al.

(10) Patent No.: US 9,744,314 B2
(45) Date of Patent: *Aug. 29, 2017

(54) AEROSOLS FOR SINUNASAL DRUG DELIVERY

(71) Applicant: PARI Pharma GmbH, Starnberg (DE)

(72) Inventors: Manfred Keller, Munich (DE); Uwe Schuschnig, Munich (DE); Johann Zimmermann, Bergheim (DE); Martin Luber, Munich (DE); Andreas Böhm, Reichling (DE)

(73) Assignee: PARI Pharma GMBH, Starnberg (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/470,197

(22) Filed: Aug. 27, 2014

(65) Prior Publication Data

US 2014/0366872 A1 Dec. 18, 2014

Related U.S. Application Data

(63) Continuation of application No. 12/675,257, filed as application No. PCT/EP2008/007090 on Aug. 29, 2008, now Pat. No. 8,852,557.

(30) Foreign Application Priority Data

Aug. 31, 2007 (EP) .................................. 07017094

(51) Int. Cl.
| | |
|---|---|
| *A61M 11/00* | (2006.01) |
| *A61K 9/00* | (2006.01) |
| *A61K 31/7052* | (2006.01) |
| *A61M 15/00* | (2006.01) |

(52) U.S. Cl.
CPC ........... *A61M 11/005* (2013.01); *A61K 9/008* (2013.01); *A61K 9/0043* (2013.01); *A61K 9/0078* (2013.01); *A61K 31/7052* (2013.01); *A61M 11/00* (2013.01); *A61M 15/0085* (2013.01)

(58) Field of Classification Search
CPC .... A61K 9/0078; A61K 9/008; A61K 9/0043; A61K 31/7052; A61M 5/0085; A61M 11/005; A61M 11/00
See application file for complete search history.

(56) References Cited

U.S. PATENT DOCUMENTS

| | | | |
|---|---|---|---|
| 5,633,006 A | 5/1997 | Catania et al. | |
| 6,705,316 B2* | 3/2004 | Blythe | A61M 15/0065 128/200.18 |
| 2005/0229927 A1 | 10/2005 | Fink et al. | |
| 2005/0244339 A1 | 11/2005 | Jauernig et al. | |
| 2006/0073173 A1 | 4/2006 | Banach et al. | |
| 2007/0181133 A1 | 8/2007 | Boehm et al. | |
| 2007/0202051 A1 | 8/2007 | Schuschnig | |

FOREIGN PATENT DOCUMENTS

| | | |
|---|---|---|
| EP | 0507707 A1 | 10/1992 |
| EP | 0546964 A1 | 6/1997 |
| EP | 1820493 A2 | 8/2007 |
| EP | 1894559 A1 | 3/2008 |
| JP | 2007-195965 A | 8/2007 |
| WO | WO-94/03225 A1 | 2/1994 |
| WO | WO-96/25918 A1 | 8/1996 |
| WO | WO-02/03998 A2 | 1/2002 |
| WO | WO2004/020029 | 3/2004 |
| WO | WO-2005/023335 A2 | 3/2005 |
| WO | WO-2005/037246 A2 | 4/2005 |
| WO | WO-2006-125132 A2 | 11/2006 |
| WO | WO-2007-090646 A1 | 8/2007 |

OTHER PUBLICATIONS

A. Boehm et al., "Investigating Drug Delivery to the Sinuses: An In Vitro Deposition Study Using a Nasal Cast Model", Respiratory Drug Delivery IX, pp. 601-604 (2004).
C. Marriott, "Once-A-Day Nasal Delivery of Steroids: Can the Nose be Tricked?", Respiratory Drug Delivery Europe, pp. 179-185 (2007).
K. Pennington et al., "The Influence of Solution Viscosity on Nasal Spray Deposition and Clearance", International Journal of Pharmaceutics, vol. 43, pp. 221-224 (1988).
J.D. Suman et al., "Comparison of Nasal Deposition and Clearance of Aerosol Generated by a Nebulizer and an Aqueous Spray Pump", Pharmaceutical Research, 16(10), pp. 1648-1652 (1999).
S. Vemuri et al., "Preparation and Characterization of Liposomes as Therapeutic Delivery Systems: A Review", Pharmaceutica Acta Helvetiae, vol. 70, pp. 95-111 (1995).
Pari Sinus—Instructions for Use, Internet citation, XP-002390675 (2006).
Pari LC Sinus Vernebler—Instructions for Use, Internet citation, XP-002390676 (2006).
Pari LC Sprint Familie—Instructions for Use, Internet citation, XP-002390677 (2005).
Japanese Abstract No. JPH08502904, filed Apr. 2, 1996, "Low Flow Rate Nebulizer, Method and Apparatus".

* cited by examiner

*Primary Examiner* — Ali Soroush
*Assistant Examiner* — Genevieve S Alley
(74) *Attorney, Agent, or Firm* — Mintz Levin Cohn Ferris Glovsky and Popeo, P.C.; Peter F. Corless

(57) ABSTRACT

A pharmaceutical aerosol is disclosed which is suitable for delivering an active compound to the mucosa of the nose, the osteomeatal complex or a paranasal sinus. The pressure of the aerosol is not constant, but pulsates at a frequency from about 10 to 90 Hz. The aerosol is further characterised in that it exhibits a low effective flow rate of less than about 5 liters per minute. The aerosol is, inter alia, suitable for the prevention, management, or treatment of a disease, symptom, or condition affecting the nose or the paranasal sinuses, such as acute and chronic sinusitis.

45 Claims, No Drawings

AEROSOLS FOR SINUNASAL DRUG DELIVERY

RELATED APPLICATIONS

This application is a continuation application of U.S. Ser. No. 12/675,257, filed Apr. 29, 2010, which is a national stage application filed under 35 U.S.C. §371 of international application no. PCT/EP2008/007090, filed Aug. 29, 2008, which claims the benefit of priority of European Application EP 07017094.9, filed Aug. 31, 2007, each of which is incorporated herein by reference in its entirety.

FIELD OF THE INVENTION

The present invention is related to pharmaceutical aerosols and to devices which are suitable for producing such aerosols. In further aspects, the invention relates to therapeutic uses of aerosols and to methods of producing them and of administering them to patients. The aerosols are suitable for delivering drug substances to selected regions within the respiratory tract, including the nasal cavity and the paranasal sinuses.

BACKGROUND OF THE INVENTION

Diseases and conditions affecting either paranasal sinuses or both the nasal cavity and the paranasal sinuses, in particular acute and chronic forms of rhinosinusitis, are increasing in incidence and prevalence in many countries and regions of the world, including Europe and the United States. These conditions may be associated with significant symptoms and have a negative impact on quality of life and daily functioning.

The method most commonly used to deliver medications to the nasal cavity is a squeeze bottle or a metering spray pump nebulising volumes of 50 to 140 µl per actuation. However, studies investigating the in vivo deposition pattern of droplets administered by a spray pump indicate that local distribution is primarily in the anterior portion of the nasal cavity leaving large portions of the nasal cavity unexposed to drug (see Suman et al., "Comparison of nasal deposition and clearance of aerosol generated by a nebulizer and an aqueous spray pump", Pharmaceutical Research, Vol. 16, No. 10, 1999). Furthermore, drugs applied by nasal pump sprays are cleared very fast from the nose, an average clearance time of between 10 and 20 minutes being accepted as normal (see C. Marriott, "Once-a-Day Nasal Delivery of Steroids: Can the Nose Be Tricked?" RDD Europe 2007, proceedings p. 179-185). The fast clearance rate of the nose and the difficulties to overcome these disadvantages by an increase of the solution viscosity have also been described by Pennington et al. ("The influence of solution viscosity on nasal spray deposition and clearance", Intern. Journal of Pharmaceutics, 43, p. 221-224, 1988). However, those attempts were only successful to improve retention of drugs in the nose prolonging the residence time, the time to clear 50% of dose, up to 2.2 hours. Consequently, the effective treatment of the nasal and paranasal mucosa via a method to increase residence time remains challenging. While the mucosa of the nasal cavity is a feasible target for locally administered drugs formulated as nasal sprays, the sinuses and the osteomeatal complex are not easily accessed by liquid formulations. In the case of relatively coarse aerosols, such as conventional nasal sprays, the deposition on the sinus mucosa is negligible, and even finer aerosols, such as those generated by nebulisers, exhibit a very low degree of sinus deposition.

The primary reason for the lack of access of an inhaled aerosol to the sinuses is anatomical: in contrast to the nasal cavity, the osteomeatal complex and the sinuses are not actively ventilated. The latter are connected to the nasal passage via small orifices called ostia, whose diameter is typically in the region of only about 0.5 to 2 mm. When air is inhaled through the nose and passes through the nasal passage into the trachea, there is only very little convective flow into the ostia.

To address the need for devices and methods which are more effective in delivering an aerosol to the osteomeatal complex and paranasal sinuses, it was suggested in WO 2005/023335 that certain particle size and vorticity characteristics must be achieved in order that a majority of an aerosolised drug formulation reaches the deep nasal cavities and the sinuses.

Furthermore, WO 2004/020029 discloses an aerosol generator comprising a nebuliser and a compressor which delivers a vibrating stream of air to the nebuliser. The document further describes that the aerosol emitted from the nebuliser should be inhaled through one nostril via an appropriate nosepiece, and that the other nostril should be closed by an appropriate device.

However, it has been found by the inventors that these teachings of the prior art do not actually ensure the deposition of a large fraction of the active agent on the sinunasal mucosa, depending on the actual configuration of the devices and the aerosol characteristics.

A substantial further improvement was achieved through the teaching of EP 1 820 493 A2 according to which the sinunasal deposition of a vibrating aerosol can be significantly increased if it is ensured that the pressure fluctuation maintains a certain amplitude, such as at least about 5 mbar.

Nevertheless, since it is still only a fraction of any aerosol which can be delivered to the sinunasal target area by the methods known today, there remains a need for technical improvements allowing the fraction of active agent deposited on the sinunasal mucosa to be increased, thus providing means for an improved, and more selective, therapy of sinunasal diseases and conditions. Furthermore, there remains a need to reduce the clearance and to prolong the residence time of the drug at the target site.

It is therefore an object of the present invention to provide improved pharmaceutical aerosols which are useful for delivering active compounds to the mucosa of the paranasal sinuses or of both the nasal cavity and the paranasal sinuses. Furthermore, it is an object of the invention to provide methods for producing such aerosols.

In particular, it is an object of the present invention to increase the fraction of active agent deposited on the sinunasal mucosa by aerosol delivery and to reduce the clearance and to prolong the residence time of the active agent at that target site. Further objects will become clear on the basis of the following description and the patent claims.

SUMMARY OF THE INVENTION

In one aspect, the invention provides a method for producing a pharmaceutical aerosol for the delivery of an active compound to the mucosa of the nose, the osteomeatal complex or a paranasal sinus. The aerosol comprises a dispersed liquid phase and a continuous gas phase. The method involves the steps of (a) providing an aerosol generator adapted for emitting an aerosol at an effective flow rate of less than about 5 liters per minute; (b) providing a means for effecting a pressure pulsation of an aerosol having a frequency in the range from about 10 to about 90 Hz; (c) providing a liquid composition comprising said active compound, wherein a unit dose of the active compound is comprised in a volume of less than about 5 ml of said liquid composition; and (d) simultaneously operating said aerosol generator for nebulising said liquid composition into an aerosol at an effective flow rate of less than about 5 liters per minute and operating said means to effect a pressure pulsation of the aerosol at a frequency in the range from about 10 to about 90 Hz.

In a particular embodiment, the method is practised with an aerosol generator that emits the aerosol at an effective flow rate of not more than about 3 liters per minute. A useful aerosol generator may include a nebuliser selected from the group consisting of ultrasonic nebulisers and electronic vibrating membrane nebulisers. The means for effecting a pressure pulsation of an aerosol is particularly useful if it is capable of maintaining an amplitude of pressure pulsation of at least about 5 mbar, or even of at least about 10 mbar.

In a further aspect, the invention provides a pharmaceutical aerosol for delivering an active compound to the mucosa of the nose, the osteomeatal complex or a paranasal sinus. The aerosol comprises a dispersed liquid phase and a continuous gas phase. The pressure of the aerosol pulsates with a frequency in the range from about 10 to about 90 Hz. Moreover, the aerosol is characterised by a low effective flow rate. In particular, the effective flow rate is less than about 5 liters per minute.

The active compound may be selected from various therapeutic categories, such as from any anti-inflammatory compounds, anti-allergies, antibiotics, antibodies, antifungals, anti-infective agents, antioxidants, antiseptics, antivirals, cytostatics, decongestants, genes, glucocorticoids, immunomodulators, leucotriene antagonists, local anaesthetics, mucolytics, oligonucleotides, peptides, plant extracts, proteins, vaccines, vitamins, and wound healing agents.

In a further aspect, the invention provides an apparatus for generating a pharmaceutical aerosol for the delivery of an active compound to the mucosa of the nose, the osteomeatal complex or a paranasal sinus. The apparatus comprises an aerosol generator which is adapted for emitting an aerosol at an effective flow rate of less than about 5 liters/min and a means for effecting a pressure pulsation of an aerosol having a frequency in the range from about 10 to about 90 Hz.

In a particular embodiment, the aerosol generator is adapted for emitting an aerosol at an effective flow rate of not more than about 3 liters/min. Optionally, the aerosol generator includes a nebuliser selected from the group consisting of ultrasonic nebulisers and electronic vibrating membrane nebulisers.

The aerosol and the apparatus of the invention may be used for the prevention, management, or treatment of any lower or upper respiratory tract disease, or of any symptom or condition caused by any lower or upper respiratory tract disease.

The method, aerosol, and apparatus of the invention as described herein achieve a high deposition of active compound in the nasal cavities and/or paranasal sinuses. Thus, they may be used for the prevention, management, or treatment of any disease, symptom, or condition affecting the nose, the sinuses and/or the osteomeatal complex, such as asthma, acute and chronic sinusitis, such as allergic sinusitis, seasonal sinusitis, bacterial sinusitis, fungal sinusitis, viral sinusitis, frontal sinusitis, maxillary sinusitis, sphenoid sinusitis, ethmoid sinusitis, vacuum sinusitis; acute and chronic rhinitis, such as allergic rhinitis, seasonal rhinitis, bacterial rhinitis, fungal rhinitis, viral rhinitis, atrophic rhinitis, vasomotor rhinitis; any combination of rhinitis and sinusitis (i.e. rhinosinusitis); nasal polyps, nasal furuncles, epistaxis, wounds of the nasal or sinunasal mucosa, such as after injury or surgery; and dry nose syndrome; nasal or sinunasal conditions caused by lower respiratory tract diseases such as cystic fibrosis. Moreover, they may be used for the administration of vaccines, antibodies and genes.

In particular, the invention provides an improvement in nasal and paranasal treatment by reducing the clearance and increasing the residence time of the drug at the target site. This aspect is a huge advantage, since a larger fraction of the dose is deliverable to the target site and dosing frequency can be reduced since the drug will be cleared much slower compared to currently established treatment regimes.

Further embodiments of the invention will become obvious on the basis of the following detailed description, the examples and the claims.

DETAILED DESCRIPTION OF THE INVENTION

In one aspect, the invention provides a pharmaceutical aerosol for the delivery of an active compound to the mucosa of the nose, the osteomeatal complex or a paranasal sinus comprising a dispersed liquid phase and a continuous gas phase. The pressure of the aerosol pulsates with a frequency in the range from about 10 to about 90 Hz. Moreover, the aerosol is characterised by a low effective flow rate. In particular, the effective flow rate is less than about 5 liters per minute.

An aerosol is a dispersion of a solid or liquid phase in a gas phase. The dispersed phase, also termed the discontinuous phase, is comprised of multiple solid or liquid particles. Typically, the particle size of the dispersed phase is less than about 100 μm, and more commonly considerably less than that. In general, both basic physical types of aerosols, i.e. solid and liquid dispersions in a gas phase, may be used as pharmaceutical aerosols. Examples of aerosols representing solid particles in a gas phase are those emitted by dry powder inhalers (DPI's). In contrast, pressurised metered-dose inhalers and nebulisers deliver aerosols whose dispersed phase is liquid.

According to the present invention, the aerosol comprises a dispersed liquid phase and a continuous gas phase. Such aerosols are sometimes referred to as "liquid aerosols" or, probably more appropriately, aerosolised liquids. It should be noted that the requirement of a dispersed liquid phase does not exclude the presence of a solid phase. In particular, the dispersed liquid phase may itself represent a dispersion, such as a suspension of solid particles in a liquid.

The continuous gas phase may be selected from any gas or mixture of gases which is pharmaceutically acceptable. For example, the gas phase may simply be air or compressed air, which is most common in inhalation therapy using nebulisers as aerosol generators. Alternatively, other gases and gas mixtures, such as air enriched with oxygen, or mixtures of nitrogen and oxygen may be used. Most preferred is the use of air as continuous gas phase.

An active compound is a natural, biotechnology-derived or synthetic compound or mixture of compounds useful for the diagnosis, prevention, management, or treatment of a disease, condition, or symptom of an animal, in particular a human. Other terms which may be used as synonyms of active compound include, for example, active ingredient, active pharmaceutical ingredient, drug substance, drug, and the like.

The aerosol of the invention is for the delivery of an active compound to the mucosa of the nose, the osteomeatal complex or a paranasal sinus. The paranasal sinuses consist of four pairs of air-filled cavities or spaces within the bones of the skull and face. They are divided into subgroups which are named according to the bones they lie under: (1) the maxillary sinuses, also called the antra, which are located under the eyes, in the upper jawbone; (2) the frontal sinuses, which lie above the eyes, in the bone of the forehead; (3) the ethmoid sinuses, positioned between the nose and the eyes, backwards into the skull; and (4) the sphenoid sinuses, which are more or less in the centre of the skull base. While the primary function of the sinuses is not entirely clear, it appears that they decrease the relative weight of the front of the skull, warm and humidify the inhaled air before it reaches the lungs, increase the resonance of the voice, and perhaps provide a buffer against blows to the face.

The nasal cavity and the paranasal sinuses are lined with mucosa. Mucosae, or mucous membranes, are mucus-covered epithelial linings. The mucosae of the nasal cavity and the paranasal sinuses are often affected by conditions such as allergies and infections, and the aerosol of the invention provides improved means to deliver therapeutically useful active agents to these membranes.

One of the key features of the aerosol is that it pulsates, or vibrates, with a selected frequency. As used herein, the pulsation of an aerosol is understood as a periodic change of pressure. Preferably, the pulsation is regular, i.e. the time interval between pressure peaks is approximately constant. The amplitude of pressure pulsation may also be relatively constant, at least with regard to the generation and emission of the pulsating aerosol from the aerosol generator.

As used herein, an aerosol generator is a device or a combination of devices capable of generating and emitting an aerosol. According to the present invention, the device is capable of aerosolising a liquid material into a dispersed liquid phase. Typically, such device is referred to as a nebuliser. Depending on the type and model of the device, the aerosol generator of the invention may require or include a compressor. In other words, the term aerosol generator is used for the complete apparatus or assembly required to produce and emit an aerosol and to administer the aerosol to an animal, such as to a human patient.

According to the invention, the pressure of the aerosol pulsates with a frequency in the range from about 10 Hz to about 90 Hz. According to some further embodiments, the pressure may also pulsate at a frequency of at least about 15 Hz, at least about 20 Hz, at least about 25 Hz, or at least about 30 Hz, respectively. At the same time, the pulsation frequency may be selected to be not higher than about 80 Hz, about 70 Hz, about 60 Hz, or about 55 Hz, respectively. Examples of useful vibration frequencies are about 36 Hz, about 40 Hz, and about 44 Hz.

It has been found that a vibrating aerosol enters the paranasal sinuses after nasal inhalation to a much larger extent than a conventional aerosol having a substantially constant pressure, provided that appropriate particles sizes are selected. Larger particle sizes will lead to little sinus deposition, but to a large deposition on the nasal mucosa, whereas very small particle sizes allow the aerosol droplets to enter the sinuses following the pressure gradient of a pressure pulse, but also to exit from the sinuses again without being deposited therein.

The principle of generating and applying a pulsating or vibrating aerosol for enhanced sinus deposition has recently been found and described, for example, in EP 0 507 707 A1 and WO 2004/020029, whose entire disclosures are incorporated herein by reference.

The paranasal sinuses are, under normal circumstances, poorly ventilated during breathing. Most of the air exchange of the sinuses occurs through the diffusion of air through the ostia, whereas little or no convective flow is observed. If an aerosol, such as a therapeutic aerosol generated by a conventional nebuliser, is inhaled through the nose, the aerosol will flow through the nasal cavity to the lower respiratory tract, if it comprises particles with an appropriately small diameter. Since there is virtually no active flow into the paranasal sinuses, very little or almost none of the aerosol is deposited therein.

In contrast, an aerosol which vibrates creates periodic transient pressure gradients extending from the actively ventilated nasal cavity through the ostia to the sinuses, which gradients cause a short period of convective flow of air and aerosol into the sinuses until the pressure therein has become equal to the air pressure in the nasal cavity. A portion of the aerosol droplets which thus enter the paranasal sinuses are deposited therein onto the mucosa. The extent to which the aerosol is deposited depends e.g. on the droplet size. For example, very small droplets, such as droplets below 1 μm, are likely to be expelled from the sinuses during the subsequent pulsation phase in which the aerosol pressure, and thus the pressure in the nasal cavity, is lower than the pressure within the sinuses, and during which a convective flow of air from the sinuses to the nasal cavity occurs.

The pressure vibration may be generated by means which are per se known. For example, WO 2004/020029 discloses a device capable of generating such vibration by means of a pressure chamber which is sealed on one side with a membrane. The membrane is moved back and forth by the action of a piston, thus periodically increasing and decreasing the internal volume of the pressure chamber, which leads to a corresponding pressure fluctuation. Via an outlet, the pressure fluctuations can be transmitted e.g. to a nebuliser where they can be superimposed on the main aerosol flow. Alternatively, the pressure fluctuations can be transmitted to the patient separately from the main aerosol flow, e.g. through a tube which is connected via a nosepiece to one of the nostrils, while the aerosol emitted from a nebuliser is introduced to the other nostril, which also leads to the same effect, i.e. the vibration of the aerosol.

In a further embodiment, the pressure of the aerosol pulsates with an amplitude of at least about 5 mbar. It has been found that, depending on the individual sinunasal anatomy of a human person, the pressure amplitude of a pulsating aerosol may be attenuated substantially, such as by large sinus volumes. According to this particular embodiment, however, a means for effecting the pressure fluctuations is used which is adapted to maintain a pressure amplitude of at least 5 mbar as measured in the nasal cavity, irrespective of the individual anatomy of the patient. Alternatively, the amplitude of vibration may be maintained at a level of at least about 10 mbar, or at least about 15 mbar, or at least about 20 mbar, or at least about 25 mbar. Further examples of useful amplitudes are from about 20 to about 50 mbar, or from about 30 to about 50 mbar, such as about 40 mbar. Even higher amplitudes than 50 mbar might be useful for certain patients and indications in which some degree of discomfort to the patients may be found acceptable, such as serious diseases and affections of the sinus mucosae.

In order to transmit effectively the aerosol pulsation to the nasal cavity it, is useful to instruct the respective patient to observe an appropriate inhalation technique. In particular, the aerosol may be introduced through one nostril via a nosepiece which seals the nostril from the external air. If the main aerosol flow itself vibrates, it is useful to add a resistance means to the exit nostril, such as an appropriate nosepiece or nose plug, in order to maintain a high pressure amplitude of the pulsating aerosol in the nasal cavities, as is described in WO 2004/020029. Alternatively, if the aerosol which is emitted from the nebuliser does not vibrate and the pressure fluctuations are separately transmitted to the patient, it is useful to transmit them also via a nosepiece which seals the nostril from the external air. Thus, the aerosol is introduced into one of the nostrils and the pressure fluctuations are introduced via the other nostril, resulting in an aerosol which vibrates within the upper respiratory tract of the patient. Moreover, it is recommended that the person receiving the aerosol closes the soft palate in order to prevent the aerosol from entering the oral cavity. The patient may be specifically instructed to hold his breath during administration of the vibrating aerosol.

The aerosol of the invention is further characterised in that it exhibits an effective flow rate of less than about 5 liters per minute. It has been surprisingly found by the inventors that the selection of a low flow rate substantially contributes to a high aerosol deposition in the sinunasal region of the respiratory system. In particular, the combination of the principle of aerosol vibration with the use of a low aerosol flow results in a marked increase in sinunasal deposition compared to conventional forms of aerosol administration.

As used herein, the effective aerosol flow is understood as the flow of the aerosol as it enters the respiratory system of a patient, e.g. through a nostril via a nosepiece. For example, during normal breathing, the healthy adult person inhales air with a typical average flow rate in the region of about 15 liters per minute.

It is noted that most jet nebulisers would probably not be suitable for providing a low effective aerosol flow of less than about 5 liters per minute. Based on their principle of aerosol generation, they require a supply of air or gas which must be above a certain operational threshold. Typically, this flow is supplied by a compressor. In the prior art, a pressure vibration is superimposed onto the main aerosol flow emitted from a jet nebuliser through a vibrating stream of air which also has a positive net flow in order to prevent that the aerosol is sucked into the tube through which the vibrations are transmitted. The net air flow, which may be in the region of about 2 liters per minute, is added to the flow rate of the main aerosol to obtain an estimate of the effective aerosol flow as defined above. For example, the effective aerosol flow rate generated by the PARI Sinus™ jet nebuliser and compressor combination is approximately 7 liters per minute. (A. Boehm et al.: Investigating drug delivery to the sinuses: An in vitro deposition study using a nasal cast model. Proceeding Respiratory Drug Delivery IX, 2004, pp 601-604).

In further embodiments of the present invention, the effective aerosol flow is selected to be not more than about 4.5 liters per minute, and not more than about 3 liters per minute, respectively. Moreover, the effective air flow may be in the region from about 0.5 to about 4.5 liters per minute, or from about 0.8 to about 4.5 liters per minute, or from about 0.8 to about 3 liters per minute, such as about 1, 2, 3, or 4 liters per minute. Aerosols exhibiting such low effective flow rates may be produced by nebulisers which do not require a stream of air or gas for nebulising a liquid. For example, ultrasonic nebulisers and electronic vibrating membrane nebulisers are suitable devices for carrying out the invention.

In a particular embodiment, the aerosol is provided in such a way that the effective aerosol flow is not constant. Non-constant aerosol flow, such as intermittent aerosol flow, is an alternative means to reconcile the need for delivering an aerosolised medicine to a target site, e.g. the mucosa of the sinunasal region, which delivery inherently requires some aerosol flow, with the need for a long aerosol retention time once it has reached the upper respiratory system in order to enable its entry into sinuses and its deposition on the target tissue. According to this embodiment, the aerosol is delivered at a first effective flow rate which is larger than zero for a first time period, followed by a time period in which a second flow rate is used, which second flow rate is substantially lower than the first flow rate, or even about zero (i.e. without any flow). In this context, the expressions "first" and "second" flow rate only mean that the flow rates are selected independently, and thus may differ from each other, but they do not necessarily specify a sequence; it is of course possible that the initial phase of providing the aerosol is a phase of low flow, followed by a phase of higher flow. It is preferred, however, that a phase of low or zero flow typically follows a phase of higher flow.

For example, the aerosol flow may be provided in an intermittent form, wherein phases of aerosol flow are interrupted by phases of very low or even absent aerosol flow. According to the present invention, it is required that at least the phases of low flow exhibit an effective flow rate as specified herein-above, i.e. of less than about 5 liters per minute, and in particular less than about 4.5 liters per minute, such as in the range from about 0.5 to about 4.5 liters per minute, or from about 0.8 to about 4.5 liters per minute, or from about 0.8 to about 3 liters per minute, such as about 1, 2, 3, or 4 liters per minute. On the other hand, the phases of (higher) aerosol flow may optionally exhibit any useful effective aerosol flow rate; even higher effective flow rates than 5 liters per minute are possible. In many cases, however, substantially smaller flow rate will also suffice. In a particular embodiment, the aerosol exhibits alternating phases of substantially absent effective aerosol flow and of effective aerosol flow of about 1 to about 10 liters per minute.

In the case of non-constant aerosol flow, the duration of the phases of (higher) aerosol flow and low or absent aerosol flow, respectively, may be independently selected. The phase of (higher) aerosol flow may have a duration which ensures that the sinunasal region, which typically has a volume of about 15 to 30 ml in adults, is filled with another portion of the aerosol after every phase or interval of aerosol flow. To accomplish this, the duration of the phase may be adjusted in consideration of the effective flow rate during this phase. For example, if the effective flow rate is 5 liters per minute, 25 ml of aerosol are transported within about 0.3 seconds. On the other hand, if the effective flow rate is 0.5 liters per minute, this would take about 3 seconds. Of course, it may also be possible to transport more or less aerosol than 15 to 30 ml within the course of one phase of flow.

The duration of the phase of lower or absent aerosol flow may, for example, be in the range from about 1 millisecond to about 10 seconds, or from about 10 milliseconds to about 3 seconds. In further embodiments, the duration is from about 0.1 to about 2 seconds, or from about 0.5 to about 2 seconds. The duration may be the same as that of the phase of (higher) aerosol flow, or shorter or longer. In a particular embodiment, the duration of the phase of lower or absent aerosol flow is at least as long as that of the phase of (higher) aerosol flow.

In the case of non-constant aerosol flow, it is not essential that the aerosol vibrates or pulsates during both the phases of low or absent and of higher aerosol flow. However, it appears necessary that it vibrates at least during some parts of some or all of the phases of low or absent aerosol flow. In one of the particular embodiments, the aerosol exhibits alternating phases of substantially absent effective aerosol flow during which the pressure of the aerosol pulsates and of an effective aerosol flow which is substantially different from zero during which the aerosol does not pulsate. In a further particular embodiment, the aerosol pulsates during both alternating phases.

Moreover, it has also been found by the inventors that the aerosol of the invention can be delivered efficiently in spite of the relatively low effective flow rate, or even in spite of intermittent aerosol flow if that feature is used. This is particularly true for a further embodiment according to which an aerosol having a high density is used. As understood herein, an aerosol having a high density is an aerosol with a high content of dispersed liquid phase, either expressed in volume or weight, per volume of continuous gas phase. For example, a useful aerosol may be selected to have a density of at least about 0.05 µl/ml, or of at least about 0.075 µl/ml, or of at least about 0.1 µl/ml, or even higher, such as in the range from about 0.1 to about 1 µl/ml. This is in contrast to conventional nebulisation for sinunasal delivery by means of a vibrating aerosol generated with a jet nebuliser, which typically leads to aerosols having a density of less than about 0.03 µl/ml.

Aerosols having a high density can be generated, for example, by some modern electronic nebulisers using the principle of a vibrating perforated mesh or membrane, such as the PARI eFlow™. Certain other types of nebulisers, such as ultrasonic nebulisers, may also be able, or may be adapted, to deliver such dense aerosols.

According to another embodiment, the volume of the liquid which comprises a unit dose and the output rate of the aerosol generator are selected in such a way that the administration time of a unit dose is not more than about 30 minutes, and more preferably not more than about 20 minutes. According to other embodiments, the administration time is not more than about 15 minutes, not more than about 12 minutes, and not more than about 10 minutes, and not more than about 5 minutes, respectively. For example, if the liquid composition is formulated to contain a unit dose within a particularly low volume, preferably less than about 2.5 ml, such as about 2 ml, and the output rate of the aerosol generator is particularly high, such as at least about 0.2 g/min, these short—and even shorter—administration times can be achieved, such as about 3 minutes or less.

For the avoidance of misunderstandings, it is pointed out that in common practice, the nominal unit dose is not completely aerosolised by aerosol generators such as jet nebulisers driven by air compressors, due to the typically presence of a dead volume in the nebuliser. The residual liquid in the device is often in the range from about 0.5 to about 1 ml. Therefore, the actually emitted volume of aerosolised liquid is less than the volume of liquid filled into the device, and—again according to common practice—the actually emitted dose of the active ingredient is less than the nominal dose filled into the device. Therefore, the time values given herein for the preferred duration of administering a unit dose should be understood as referring to the duration of aerosolising that fraction of the unit dose formulation which is actually emitted, excluding the fraction of the liquid and of the drug substance which is lost as a residue in the device. When using electronic mesh and/or perforated vibrating mesh nebulisers, the residual volumes can be kept close to zero, which is why smaller volume fills from 0.1 to 2 ml and more often 0.3 to 1.2 ml may be favourably selected.

In a further embodiment, the aerosol of the invention exhibits a mass median diameter (MMD) of the dispersed liquid phase in the range from about 2.0 to about 6 µm, as measured by laser diffraction. Various appropriate analytical apparatuses to determine the mass median diameter are known and commercially available, such as the Malvern MasterSizer X™ or Malvern SprayTec™. The geometric distribution of the aerosolised liquid particles or droplets may be determined simultaneously with the mass median diameter and represents the width of the droplet size distribution.

While the mass median diameter should be rather small, such as less than about 3 µm, or even less than about 2 µm, if the deep lung is the targeted site of aerosol delivery, such as in those cases where systemic absorption of an active compound through the lungs is desired, it has been found that the most useful diameter for depositing the aerosol in the nasal cavity and in the paranasal sinuses may be somewhat larger. For example, an MMD in the region of 3 to 3.5 µm does not seem very desirable for pulmonary delivery, but may be suitable for sinus delivery. Furthermore, it is suggested that the MMD which will lead to the relatively largest aerosol deposition may also depend on individual factors, in particular on the geometry of the paranasal sinuses including the ostia through which the aerosol reaches the sinuses. For example, the volume of the sinuses and the diameter of the ostia differ substantially between individuals. A larger diameter of the ostia is believed to favour the entrance of larger aerosol droplets into the sinuses, even though the diameters of the ostia and of the droplets are of completely different magnitudes. If the individual sinunasal anatomy, or a parameter derived therefrom, of a person to be treated with an aerosol is at least partially known, it may even be possible to select a particular MMD for optimised nasal or sinunasal delivery. In some embodiments, the aerosol of the invention may have a mass median diameter of about 2.5 to 4.5 µm, in others from about 3 to about 4 µm, or from about 2.8 to about 3.5 µm, respectively. In further embodiments, the MMD is approximately (±0.2 µm) 2.8 µm, 3.0 µm, 3.2 µm, 3.4 µm, 3.6 µm, 3.8 µm, or 4.0 µm.

In a further embodiment, the geometric standard deviation of the MMD of the aerosol of the invention may be selected in the range from less than 2 up to about 3, such as about 2.3 to 2.7.

The invention is practised with any aerosolisable liquid comprising an active compound which is suitable for inhalation. In addition, the formulation should be designed and processed to be pharmaceutically acceptable. Most preferably, the liquid composition should be sterile when withdrawn from its packaging container. The inactive ingredients of the liquid composition should be pharmaceutically acceptable.

The volume of the dispersed liquid phase may be selected so that a unit dose of the active compound is contained in not more than about 5 ml. In particular, the volume comprising a unit dose may be less than about 2.5 ml, such as about 2 ml, about 1.5 ml, about 1 ml, about 0.5 ml or about 0.25 ml.

It has been found that, in contrast to pulmonary aerosol therapy in which the administration of 5 ml of liquid phase are not uncommon, a better chance for the delivery of a higher portion of the drug contained in the aerosol to mucosa of the nasal cavity and the paranasal sinuses is achieved by selecting relatively low volumes. Without wishing to be bound by theory, this effect is believed to be related to a limited capacity of particularly the paranasal mucosae to hold the deposited aerosol. In other words, the higher the volume of the liquid phase administered to the target mucosae, the higher the likelihood that a substantial fraction of the aerosol will be drained or discharged before it can become effective. Thus it is possible that higher volumes change the distribution pattern of the deposited aerosol: if a small volume, such as 1 ml of liquid phase, is deposited onto the sinunasal mucosae according to a certain useful or desirable pattern, such pattern may be altered substantially if the volume is increased to 5 ml or more.

In further preferred embodiments, the volume of the dispersed liquid phase is about 4 ml or less, 3.5 ml or less, 3 ml or less, 2.5 ml or less, or in the range from about 0.25 to about 3 ml, or in the range from about 0.5 to about 3 ml, or from about 1 to about 2.5 ml. It should be noted that, in calculating the volume of the liquid phase which is aerosolised, many of the currently available aerosol generators have a dead volume of up to about 1 ml, some of them even more than 1 ml, so that a larger volume of liquid must be filled into the fluid feed of the device to obtain a certain volume of aerosolised liquid.

The liquid composition may of course comprise further excipients, such as one or more solvents, co-solvents, acids, bases, buffering agents, osmotic agents, stabilizers, antioxidants, taste-masking agents, clathrate- or complex-forming compounds, polymers, flavours, sweetening agents, ionic and non-ionic surfactants, thickeners, colouring agents, fillers, and bulking agents.

Solvents and co-solvents, other than water, should be avoided if possible if the composition is intended for inhalation. If the incorporation of a solvent cannot be avoided, the excipient should be selected carefully and in consideration of its physiological acceptability. For example, if the composition is designated for the treatment of a life-threatening disease, the use of some limited amount of ethanol, glycerol, propylene glycol or polyethylene glycol as a non-aqueous solvent may be acceptable. According to the presently more preferred embodiments, however, the composition is substantially free of these solvents, and in particular of glycerol, propylene glycol or polyethylene glycol.

In order to provide a well tolerated aerosol, the preparation should be adjusted to a euhydric pH value. The term "euhydric" already implies that there may again be a divergence between pharmaceutical and physiological requirements so that a compromise has to be found which, for example, guarantees that the preparation is, from an economical point of view, just sufficiently stable during storage but, on the other hand, largely well tolerated. Preferably, the pH value lies in the slightly acidic to neutral region, i.e., in the range of pH values of about 3.5 to 8.5. It is to be noted that deviations towards a weakly acidic environment can be tolerated better than shifts of the pH value into the alkaline region. A pH value in the range of about 4.5 to about 7.5 is particularly preferred.

For adjusting and, optionally, buffering pH value, physiologically acceptable acids, bases, salts, and combinations of these may be used. Suitable excipients for lowering the pH value or as acidic components of a buffer system are strong mineral acids, in particular, sulphuric acid and hydrochloric acid. Moreover, inorganic and organic acids of medium strength as well as acidic salts may be used, for example, phosphoric acid, citric acid, tartaric acid, succinic acid, fumaric acid, methionine, acidic hydrogen phosphates with sodium or potassium, lactic acid, glucuronic acid etc. However, sulphuric acid and hydrochloric acid are most preferred. Suitable for raising the pH value or as basic component for buffer system are, in particular, mineral bases such as sodium hydroxide or other alkali and alkaline earth hydroxides and oxides such as, in particular, magnesium hydroxide and calcium hydroxide, ammonium hydroxide and basic ammonium salts such as ammonium acetate, as well as basic amino acids such as lysine, carbonates such as sodium or magnesium carbonate, sodium hydrogen carbonate, citrates such as sodium citrate etc.

In one of the preferred embodiments, the liquid composition contains a buffer system consisting of two components, and one of the preferred buffer systems contains citric acid and sodium citrate. Nevertheless, other buffering systems may also be suitable.

Not primarily for physiological, but for pharmaceutical reasons, the incorporation of one or more excipients to achieve chemical stabilisation may be required. This depends mainly on the kind of the active agent contained therein. The most common degradation reactions of chemically defined active agents in aqueous preparations comprise, in particular, hydrolysis reactions, which may be limited, primarily, by optimal pH adjustment, as well as oxidation reactions. Examples for active agents which may be subject to oxidative attack are those agents that have olefinic, aldehyde, primary or secondary hydroxyl, ether, thioether, endiol, keto or amino groups. Therefore, in the case of such oxidation-sensitive active agents, the addition of an antioxidant, optionally in combination with a synergist, may be advisable or necessary.

Antioxidants are natural or synthetic substances which prevent or interrupt the oxidation of the active agents. These are primarily adjuvants which are oxidisable themselves or act as reducing agents, such as, for example, tocopherol acetate, reduced glutathione, catalase, peroxide dismutase, butylhydroxyansiol (BHA). Synergistic substances are, for example, those which do not directly act as reactants in oxidation processes, but which counteract oxidation by an indirect mechanism such as the complexation of metal ions which act catalytically in the oxidation, which is the case, for example, for EDTA derivatives (EDTA: ethylenediamine tetraacetic acid). Further suitable antioxidants are ascorbic acid, sodium ascorbate and other salts and esters of ascorbic acid (for example, ascorbylpalmitate), fumaric acid and its salts, malic acid and its salts, butyl hydroxy anisole, propyl gallate, as well as sulphites such as sodium metabisulfite. Apart from EDTA and its salts, citric acid and citrates, malic acid and its salts and maltol (3-hydroxy-2-methyl-4H-pyran-4-one) may also act as chelating agents.

In one of the embodiments, the composition contains at least one antioxidant. In a further embodiment, it contains both an antioxidant and a chelating agent. The combination of a vitamin E derivative, in particular, vitamin E acetate, with an EDTA derivative, in particular, EDTA disodium salt, is particularly preferred. In the case of certain active agents, this combination has proven to be particularly advantageous for obtaining high chemical stability and durability of the composition. In particular, in combination with the active agent budesonide, this combination of excipients is preferred.

In order to be well-tolerated, an aerosol should, as far as possible, have a physiologic tonicity or osmolality. Thus, it may be desirable to incorporate an osmotically active excipient to control the osmolality of the aerosol. The content of this excipient (or excipients, if a combination of substances is used) should be selected to yield an osmolality of the aerosol which does not deviate too much from that of physiological fluids, i.e., from about 290 mOsmol/kg. However, in individual cases, a compromise has again to be found between the physical-chemical or pharmaceutical needs on one hand and the physiological requirements on the other hand. Furthermore, it is believed that sinunasal aerosol delivery is not as problematic in terms of osmolality as, for example, deep lung delivery of aerosols. In general, an osmolality in the range of up to 1200 mOsmol/kg may be acceptable. In particular, an osmolality in the range of about 200 up to about 600 mOsmol/kg is preferred. In further embodiments, the osmolality is even closer to the physiological value, i.e. from about 220 to about 400 mOsmol/kg.

If the active agent and the surfactants contained in the composition give an osmolality below the required or desired value it can be adjusted to the desired value by the addition of one or more suitable osmotically active excipients. Such compounds are, in particular, innocuous mineral salts which react largely neutrally (unless such adjuvants are, at the same time to adjust or buffer the pH value), such as sodium, calcium or magnesium chloride, sulfate or phosphate. One of the particularly preferred members of these is sodium chloride. Further preferred excipients for this purpose are magnesium and calcium sulfate and chloride.

As an alternative to the neutral mineral salts, physiologically safe organic compounds may be used as isotonising agent. Particularly suitable are water soluble substances with a relatively low molecular weight, for example, with a molecular weight of less than 300 or, better still, less than 200 and with a correspondingly high osmotic activity. Examples for such excipients are sugars, such as trehalose, lactose, fructose, sucrose, glucose and sugar alcohols, in particular, mannitol, xylitol, sorbitol and isomaltol.

Among the optional excipients are preservatives, which may be considered less desirable for aerosols which are for inhalation. Therefore, in one of the embodiments, the composition is substantially free of preservatives. However, if the composition, or a medicament comprising the composition, is to be packaged in multiple unit dose containers, it may be necessary that a preservative is used in order to maintain sterility.

In one of the preferred embodiments, the liquid from which the aerosol of the invention is obtained is provided in aqueous liquid form. Alternatively, it may be provided in the form of a dry solid material which is adapted for preparing an aqueous liquid which can be administered as an aerosol. If the chemical and physical stability of the active agent and the composition permit, it is preferred that the composition is provided in liquid form. If an acceptable shelf life cannot be achieved, the composition must be formulated as a dry solid, such as a powder or lyophilisate for reconstitution.

As used herein, aqueous liquids are liquid compositions in which the liquid carrier or solvent consists predominantly of water, or at least 50 wt.-% of which represent water. The liquid state means that the preparation is either a liquid single-phase system or a multi-phase system but having a continuous liquid phase. Thus, the aqueous liquid according to the invention may represent an aqueous solution, a colloidal solution, a suspensions or an emulsion.

Even though the liquid carrier is predominantly water, it may, in individual cases, contain one or more liquids which are at least partially miscible with water, such as ethanol, glycerol, propylene glycol or polyethylene glycol. However, it is preferred that the composition is substantially free of non-aqueous liquids.

Even though the aerosolization of emulsions and suspensions is possible, the aqueous liquid preferably represents a solution, or a colloidal solution or dispersion, according to some of the embodiments of the invention. Colloidal solutions, or dispersions, are defined herein as monophasic systems, unlike e.g. suspensions which contain a dispersed solid phase. The rationale behind this is that the colloidal material dispersed within a colloidal solution or dispersion (as used herein, these are interchangeable) does not have the measurable physical properties usually associated with a solid material; furthermore, it does not provide a true solid-liquid interphase.

Colloidal carrier systems, such as micelles, mixed micelles, colloidal complexes, and liposomes, have been used in drug delivery as carriers for poorly water-soluble active compounds, or for the targeted delivery of certain drug substances.

In a colloidal system, not all components are molecularly dispersed; at least one of them is colloidally dispersed. Usually, colloidal structures are understood as being in a size range below about 1 µm, as commonly understood, or between 1 and about 500 µm as defined in other sources (H. Stricker, Physikalische Pharmazie, 3rd Edition, page 440). Therefore, colloidal structures are practically not visible with a light microscope and do not result in marked turbidity of the solution, but rather in opalescence. However, the size limits given above are not rigid since they will depend to some extent on the properties under consideration. This nomenclature can be applied to coarser systems, especially when a gradual transition of properties is considered.

According to one of the embodiments of the invention, the liquid composition which is converted into an aerosol comprises a colloidal carrier system with an average size of up to about 1 µm (as measured by photon correlation spectroscopy). In further embodiments, the average diameter is from about 10 nm to about 400 nm. In a further embodiment, it is from about 10 nm to about 250 nm.

The colloidal structures should preferably have a relatively narrow size distribution. For example, if the composition contains liposomes and if it is intended to include a step of sterile filtration in the manufacture of the composition, the average diameter of the liposomes should preferably be below about 200 nm but also rather narrowly distributed in order to allow the sterile filtration procedure without problems such as drug loss or changes in the composition due to the retention of a substantial fraction of larger liposomes. A suitable parameter describing the distribution of the diameter of the colloidal structures is the polydispersity index. It is preferred that the polydispersity index is below about 0.5. More preferably, the polydispersity index is below about 0.4. In a further embodiment, it is below 0.3, or even below 0.2 or 0.1.

A relatively low polydispersity index, reflecting a narrow size distribution, can be achieved by methods generally known to the skilled persons. For example, liposomal solutions may be sonicated, homogenized (optionally with the use of high pressure), or extruded through membranes under moderate pressure. Dialysis or centrifugation can be used as methods to isolate more narrow fractions of colloidal structures.

The respective compositions are not only characterized by the presence of colloidal structures, but also by the low content or even absence of larger particles. In particular, larger particles capable of sedimentation, or particles of solid material should preferably be absent.

If the liquid composition represents as a micellar or mixed micellar solution, it is preferred that the average size of the micelles is less than about 200 nm (as measured by photon correlation spectroscopy), such as from about 10 nm to about 100 nm. Particularly preferred are micelles with average diameters of about 10 to about 50 nm.

Methods for the preparations and characterization of liposomes and liposome preparations are known as such to the skilled person. Often, multilamellar vesicles will form spontaneously when amphiphilic lipids are hydrated, whereas the formation of small unilamellar vesicles usually requires a process involving substantial energy input, such as ultrasonication or high pressure homogenization. Further methods for preparing and characterizing liposomes have been, for example, described by S. Vemuri et al. [Preparation and characterization of liposomes as therapeutic delivery systems: a review. Pharm. Acta Helv. 1995, 70(2): 95-111].

Of the known liposomes, those are preferred according to the invention which have a predominantly colloidal size, i.e., whose average particle size lies below about 1 inn, and better still at maximally about 500 nm. Highly preferred is a diameter below about 200 nm. Such average particle size will usually allow sterile filtration through a filter with a pore size of 0.22 μm, which is a significant advantage in case the composition is not stable enough to withstand heat sterilization.

To obtain the aerosol of the invention which is suitable for nasal, paranasal sinus, or sinunasal delivery, the surface tension of the composition of the invention should preferably be adjusted to the range of about 25 to 80 mN/m, and preferably to the range of about 30 to 75 mN/m. In this context, it is to be taken into consideration that, in the lowest part of this range, a particularly good spreadability of the preparation on the mucous membranes may be expected, but that the quality of the aerosol and the efficiency of the nebulization could be adversely affected.

On the other hand, if a surfactant is incorporated in order to colloidally solubilise a poorly soluble active agent, it can hardly be avoided that the surface tension is reduced fairly markedly below that of water or physiological buffer solution. Thus, a compromise may have to be found in each case depending on the active compound and the intended application.

It has been found by the inventors that, contrary to the findings of prior art such as WO 01/02024, a surface tension which is lower than that of water or aqueous buffer solutions is not necessary for sinunasal aerosol deposition. In fact, the present inventors have found that liquid compositions having a relatively high surface tension can be effectively delivered to the mucosal surfaces of the nasal cavity and of the paranasal sinuses if the teachings of the present invention are observed. A low surface tension may be unavoidable if a surface-active drug substance or excipient is incorporated in the liquid compositions which is aerosolised, but if no surfactant is required and if the drug substance itself does not lead to a marked decrease of surface tension, it is preferred according to the present invention that the surface tension is selected in the region of about 65 to about 80 mN/m, such as in the range of approx. 70 mN/m.

The dynamic viscosity also has an influence on the particle size distribution of the aerosol formed by nebulisation and on the efficiency of nebulisation. It should preferably be adjusted to a range of about 0.8 to about 3 mPas. According to another embodiment, the dynamic viscosity is in the range of about 1.0 to about 2.5 mPas, or in the range from about 1.2 to about 2.0 mPas.

The active compound comprised in the aerosol of the invention is typically a drug substance which is useful for the prevention, management, or treatment of any disease, symptom, or condition affecting the nose, the sinuses and/or the osteomeatal complex, such as acute and chronic sinusitis, such as allergic sinusitis, seasonal sinusitis, bacterial sinusitis, fungal sinusitis, viral sinusitis, frontal sinusitis, maxillary sinusitis, sphenoid sinusitis, ethmoid sinusitis, vacuum sinusitis; acute and chronic rhinitis, such as allergic rhinitis, seasonal rhinitis, bacterial rhinitis, fungal rhinitis, viral rhinitis, atrophic rhinitis, vasomotor rhinitis; any combination of rhinitis and sinusitis (i.e. rhinosinusitis); nasal polyps, nasal furuncles, epistaxis, wounds of the nasal or sinunasal mucosa, such as after injury or surgery; and dry nose syndrome; nasal or sinunasal conditions caused by lower respiratory tract diseases such as asthma and cystic fibrosis. Alternatively, it may be a vaccine, an antigen such as an antibody, or a nucleic acid such as a gene.

Among the active compounds which may be useful for serving one of these purposes are, for example, substances selected from the group consisting of anti-inflammatory compounds, glucocorticoids, anti-allergic drugs, antioxidants, vitamins, leucotriene antagonists, anti-infective agents, antibiotics, antifungals, antivirals, mucolytics, decongestants, antiseptics, cytostatics, immunomodulators, vaccines, wound healing agents, local anaesthetics, oligonucleotides, peptides, proteins and plant extracts.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, dehydroepiandrosterone-sulfate (DHEAS), elastane, prostaglandin, leukotriene, bradykinin antagonists, non-steroidal anti-inflammatory drugs (NSAIDs), such as ibuprofen including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amiidine penicillins (mecillinam);

cephalosporins, including cefazolins (cefazolin, cefazedone); cefuroximes (cerufoxim, cefamdole, cefotiam), cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetile, cefetamet pivoxil, cefotiam hexetil), loracarbef, cefepim, clavulanic acid/amoxicillin, Ceftobiprole;

synergists, including beta-lactamase inhibitors, such as clavulanic acid, sulbactam, and tazobactam;

carbapenems, including imipenem, cilastin, meropenem, doripenem, tebipenem, ertapenem, ritipenam, and biapenem;

monobactams, including aztreonam;

aminoglycosides, such as apramycin, gentamicin, amikacin, isepamicin, arbekacin, tobramycin, netilmicin, spectinomycin, streptomycin, capreomycin, neomycin, paromoycin, and kanamycin;

macrolides, including erythromycin, clarythromycin, roxithromycin, azithromycin, dithromycin, josamycin, spiramycin and telithromycin;

gyrase inhibitors or fluroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin;

tetracyclins, including tetracyclin, oxytetracyclin, rolitetracyclin, minocyclin, doxycycline, tigecycline and aminocycline;

glycopeptides, including vancomycin, teicoplanin, ristocetin, avoparcin, oritavancin, ramoplanin, and peptide 4;

polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;

sulfonamides, including sulfadiazine, sulfamethoxazole, sulfalene, co-trimoxazole, co-trimetrol, co-trimoxazine, and co-tetraxazine;

azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals including flucytosin, griseofluvin, tonoftal, naftifin, terbinafin, amorolfin, ciclopiroxolamin, echinocandins, such as micafungin, caspofungin, anidulafungin;

nitrofurans, including nitrofurantoin and nitrofuranzone;

polyenes, including amphotericin B, natamycin, nystatin, flucocytosine;

other antibiotics, including tithromycin, lincomycin, clindamycin, oxazolindiones (linzezolids), ranbezolid, streptogramine A+B, pristinamycin aA+B, Virginiamycin A+B, dalfopristin/qiunupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine;

antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors;

antiseptics, including acridine derivatives, iodine-povidone, benzoates, rivanol, chlorhexidine, quartemary ammonium compounds, cetrimides, biphenylol, clorofene, and octenidine;

plant extracts or ingredients, such as plant extracts from chamomile, hamamelis, echinacea, calendula, thymian, papain, pelargonium, pine trees, essential oils, myrtol, pinen, limonen, cineole, thymol, mentol, camphor, tannin, alpha-hederin, bisabolol, lycopodin, vitapherole;

wound healing compounds including dexpantenol, allantoin, vitamins, hyaluronic acid, alpha-antitrypsin, anorganic and organic zinc salts/compounds, salts of bismuth and selen interferons (alpha, beta, gamma), tumor necrosis factors, cytokines, interleukines;

immunomodulators including methotrexat, azathioprine, cyclosporine, tacrolimus, sirolimus, rapamycin, mofetil; mofetil-mycophenolate.

cytostatics and metastasis inhibitors;

alkylants, such as nimustine, melphanlane, carmustine, lomustine, cyclophosphamide, ifosfamide, trofosfamide, chlorambucil, busulfane, treosulfane, prednimustine, thiotepa;

antimetabolites, e.g. cytarabine, fluorouracil, methotrexate, mercaptopurine, tioguanine;

alkaloids, such as vinblastine, vincristine, vindesine;

antibiotics, such as alcarubicine, bleomycine, dactinomycine, daunorubicine, doxorubicine, epirubicine, idarubicine, mitomycine, plicamycine;

complexes of transition group elements (e.g. Ti, Zr, V, Nb, Ta, Mo, W, Pt) such as carboplatinum, cis-platinum and metallocene compounds such as titanocendichloride;

amsacrine, dacarbazine, estramustine, etoposide, beraprost, hydroxycarbamide, mitoxanthrone, procarbazine, temiposide;

paclitaxel, iressa, zactima, poly-ADP-ribose-polymerase (PRAP) enzyme inhibitors, banoxantrone, gemcitabine, pemetrexed, bevacizumab, ranibizumab.

Examples of potentially useful mucolytics are DNase, P2Y2-agonists (denufosol), drugs affecting chloride and sodium permeation, such as N-(3,5-Diamino-6-chloropyrazine-2-carbony)-N'-{4-[4-(2,3-dihydroxypropoxy)-phenyl] butyl}guanidine methanesulfonate (PARION 552-02), heparinoids, guaifenesin, acetylcysteine, carbocysteine, ambroxol, bromhexine, tyloxapol, lecithins, myrtol, and recombinant surfactant proteins.

Examples of potentially useful vasoconstrictors and decongestants which may be useful to reduce the swelling of the mucosa are phenylephrine, naphazoline, tramazoline, tetryzoline, oxymetazoline, fenoxazoline, xylometazoline, epinephrine, isoprenaline, hexoprenaline, and ephedrine.

Examples of potentially useful local anaesthetic agents include benzocaine, tetracaine, procaine, lidocaine and bupivacaine.

Examples of potentially useful antiallergic agents include the afore-mentioned glucocorticoids, cromolyn sodium, nedocromil, cetrizin, loratidin, montelukast, roflumilast, ziluton, omalizumab, heparinoids and other antihistamins, including azelastine, cetirizin, desloratadin, ebastin, fexofenadin, levocetirizin, loratadin.

Antisense oligonucleotides are short synthetic strands of DNA (or analogs) that are complimentary or antisense to a target sequence (DNA, RNA) designed to halt a biological event, such as transcription, translation or splicing. The resulting inhibition of gene expression makes oligonucleotides dependent on their composition useful for the treatment of many diseases and various compounds are currently clinically evaluated, such as ALN-RSV01 to treat the respiratoy syncytical virus by, AVE-7279 to treat asthma and allergies, TPI-ASM8 to treat allergic asthma, 1018-ISS to treat cancer.

Examples of potentially useful peptides and proteins include antibodies against toxins produced by microorganisms, antimicrobial peptides such as cecropins, defensins, thionins, and cathelicidins.

For any of these and other explicitly mentioned examples of drug substances which are potentially useful for carrying out the invention, the compound names given herein should be understood as also referring to any pharmaceutically acceptable salts, solvates or other hydrates, prodrugs, isomers, or any other chemical or physical forms of the respective compounds comprising the respective active moieties.

However, the practice of the invention is not limited to these compounds. Any therapeutic or prophylactic substance or mixture or combination of substances having a potentially beneficial effect on the mucosa of the nasal cavity and/or of the paranasal sinuses should be understood as within the scope of the invention.

In one preferred embodiment of the invention, the active compound comprises a macrolide, such as azithromycin or clarithromycin, in a concentration of 10 to 100 mg/ml and the liquid composition comprises divalent cations, the ratio of the total molar concentration of divalent cations to the molar concentration of the macrolide being in the range of from about 0.1:1 to 10:1, for example 0.1:1, 0.5:1, 1:1, 1.5:1, 2:1, 5:1 or 10:1. Preferably, an at least equimolar amount of divalent cations (relative to the amount of macrolide) is used (i.e., the molar ratio of divalent cations to macrolide is at least 1). The divalent cations are preferably selected from water soluble inorganic and organic salts of calcium and magnesium. Surprisingly it was found that water soluble magnesium salts improve substantially the taste of dissolved azithromycin formulations for inhalation when aerosolized for instance with an eFlow™ electronic nebulizer. Furthermore, it was found that the solubility and stability upon storage of aqueous azithromycin solutions comprising water soluble magnesium or calcium salts are improved compared to formulations without magnesium and calcium salts.

In a further preferred embodiment of the invention, the active compound is a combination of azithromycin and a fluoroquinolone or an amino glycoside in a ratio in the range from 1:3 to 3:1.

In one of the embodiments, the active compound is selected from drug substances which have poor water solubility, such as a solubility in water of less than about 1 wt.-% at 20° C. In another embodiment, the solubility of the active compound, or of one of the active compounds present in the liquid phase of the aerosol, is less than about 1 mg/ml.

Poorly water-soluble active agents are generally not very easy to administer as aerosolised liquids, one of the reasons being that the volume of liquid which can be administered as an aerosol is limited. However, it has been found by the inventors that, surprisingly, such compound may be delivered in aerosolised form even to the sinunasal mucosa if the teachings and preferences disclosed herein are observed.

Poor water solubility is particularly problematic if the drug substance also requires relatively large unit doses. A unit dose is understood as the quantity of an active compound which is suitable and effective when given at one event of administration. Optionally, a unit dose, or single dose, is administered repeatedly, according to a certain regimen, such as once daily, twice daily, or three times daily, for an extended period of time, such as several days, weeks, or even longer.

If, for example, a unit dose of a drug substance is not dissolvable in 5 ml of water or of an aqueous carrier, oral administration or parenteral infusion may still be feasible because large volumes of water (or gastrointestinal fluid) are available to dissolve the compound and render it absorbable. In contrast, it is more difficult to formulate such compounds for aerosol delivery, because the volume of liquid carrier cannot be increased ad libitum. In the case of sinus or sinunasal aerosol delivery, it has been found by the inventors that unit doses having a volume of more than 5 ml lead to large losses of drug, as the nasal and sinus mucosa can only be wetted by a small amount of liquid.

While it may be difficult to formulate such compounds as aerosolisable liquid compositions for nasal and/or sinus delivery, the problems can be overcome by using drug nanoparticles, by combining the active compound with a colloidal carrier system, or by solubilising it with a solubility-enhancing agent or excipient.

In one of the embodiments, the a unit dose of the active compound requires more than about 5 ml of water to be dissolved at 20° C., and is incorporated within the liquid from which the aerosol of the invention is obtained in the form of nanoparticles, incorporated within or associated with a colloidal carrier, or in solubilised form, wherein the solubilised form is achieved through the incorporation of a solubility-enhancing agent. In other embodiments, the aqueous solubility of the active ingredient relative to its unit dose is still lower, such as requiring at least about 10 ml of water to be dissolved at 20° C., or more than about 50 ml, or even more than about 100 ml.

As used herein, nanoparticles are particles of a semisolid or solid material having a diameter in the range of up to about 1 μm. It should be noted that the solid state may be difficult to observe for such small particles, and no solid-liquid-interphase may be detectable in liquid systems comprising such nanoparticles. Nevertheless, the material from which the nanoparticles are predominantly composed is a semisolid or solid material under normal conditions. Nanoparticles may have various shapes and structures: nanospheres, nanorods, and nanocapsules are only a few examples of different types of nanoparticles. In one of the preferred embodiments, the nanoparticles have a mass median diameter of less than about 800 nm, and in a further embodiment, the mass median diameter is less than about 600 nm or even less than about 500 nm. In further embodiments, the mass median diameter is in the range from about 150 to about 450 nm. Most preferred are particles having sizes below 200 nm, which can be sterilized by a standard filtration process via about 220 nm filters.

If nanoparticles are present in the liquid phase of the aerosol, they are preferably stabilised by at least one excipient which is optionally selected from the group of surfactants, polyelectrolytes, and thickeners or gelling agents. The function of the stabiliser or stabilisers is to prevent the agglomeration, or at least the irreversible agglomeration of the nanoparticles, which have a particularly high surface energy.

Preferably, the nanoparticles are predominantly composed of the active compound, but covered with at least a layer of stabiliser molecules. Further optional features of drug nanoparticles which can be incorporated within liquid compositions which are suitable for aerosolisation are disclosed, for example, in WO 96/25918, whose teachings are incorporated herein by reference.

Colloidal carriers, or colloidal drug carriers, are structures in the colloidal size range, i.e. typically having an average diameter of less than about 1 μm, which may be primarily composed of excipient molecules. In such colloidal constructs, a drug substance may be incorporated, or an active ingredient may simply be associated with the colloidal carrier. Non-limiting examples of such colloidal carriers include liposomes, lipid complexes, micelles, mixed micelles, lipid nanoparticles, nanoparticles, nanocapsules, niosomes, and polymer conjugates. Further aspects of such colloidal systems have been described herein-above.

Optionally, the liquid phase of the aerosol comprises a poorly water-soluble active agent and a solubility-enhancing excipient, such as a surfactant, a base, an acid, or a complexing agent, such as a cyclodextrin. As used herein, a solubility-enhancing agent is an excipient or a combination of excipients whose presence in an aqueous liquid composition, such as the liquid phase of the aerosol of the invention, results in a substantially enhanced molecular or colloidal solubility of the incorporated active ingredient. In particular, a solubility-enhancing agent or excipient effects an increase in the solubility of the active compound of at least 20%. In further embodiments, the increase in solubility, whether molecular or colloidal, is at least about 50%, at least about 100%, and at least about 150%, respectively. Preferably, the solubility-enhancing agent is selected in quality and quantity to achieve that a unit dose of the active compound, which may not be dissolvable in 5 ml of water in the absence of the solubility-enhancing agent at 20° C., is now dissolved or colloidally solubilised in a liquid volume of not more than about 5 ml, and preferably in a liquid phase whose volume is not more than about 4 ml. According to another embodiment, the active agent is dissolved or colloidally solubilised in a liquid whose volume which is less than 3 ml, and preferably in a range from about 0.5 ml to about 2 ml.

Optionally, the solubility-enhancing agent adjusts the pH of an aqueous liquid composition to a value at which the active compound is better soluble. In this case, the solubility-enhancing agent is selected from the group of pharmaceutically acceptable acids and bases. As used herein, the terms acid and base include acidic and basic salts or, more generally defined, compounds whose saturated aqueous solution exhibits a pH which is substantially different from 7, such as below about 6 for acids, and above about 8 for bases.

Examples of pharmaceutically acceptable acids and bases include inorganic excipients such as ammonium salts, sodium hydroxide, magnesium hydroxide, calcium hydroxide, sulphuric acid, hydrochloric acid, phosphoric acid; and organic compounds such as lysine, methionine, arginine, citric acid, and fumaric acid.

Alternatively, the solubility-enhancing agent is a pharmaceutically acceptable surfactant. Surfactants are amphiphilic, surface- or interface-active materials. Such compounds have at least one relatively hydrophilic and at least one relatively hydrophobic, or lipophilic, molecular region. They accumulate at phase interfaces and reduce surface tension. Surfactants are often used, inter alia, in order to stabilize multi-phase systems. Non-ionic surfactants are surfactants which have no real ionic charge in aqueous media at substantially neutral pH (for example, between pH 4 and 10), but, at most, partial charges. A surfactant may also be referred to as a detergent or tenside, or, to denote its function in particular compositions, as an emulsifier or wetting agent.

Suitable non-ionic surfactants include, in particular, those which are to be considered safe for oral or nasal inhalation or oromucosal administration. Examples of non-ionic surfactants which appear to have a particularly good physiological compatibility are tyloxapol, polysorbates such as polysorbate 80, vitamin E-TPGS, and macrogol hydroxystearates such as macrogol-15-hydroxystearate.

Optionally, more than one surfactant may be present in the liquid phase which is aerosolised, such as polysorbate 80 in combination with vitamin E-TPGS. It has been observed that the effect of surfactants on the properties of the composition, in particular the solubilising effect on poorly soluble active agents, can be additive. This means that by incorporating two surfactants instead of only one can achieve a desired effect on the formulation at a lower concentration of each of the surfactants, which may be useful to avoid the occurrence of adverse effects caused by a higher content of only one particular surfactant.

Phospholipids are an example of ionic surfactants. They may be defined as amphiphilic lipids which contain phosphorus. Also known as phosphatides, they play an important role in nature, in particular, as double layer-forming constituents of biological membranes. Phospholipids which are chemically derived from phosphatidic acid occur widely and are also commonly used for pharmaceutical purposes. This acid is a usually (doubly) acylated glycerol-3-phosphate in which the fatty acid residues may be of different length. The derivatives of phosphatidic acid include, for example, the phosphocholines or phosphatidylcholines, in which the phosphate group is additionally esterified with choline, furthermore phosphatidyl ethanolamines, phosphatidyl inositols etc. Lecithins are natural mixtures of various phospholipids which usually have a high proportion of phosphatidyl cholines. Depending on the source of a particular lecithin and its method of extraction and/or enrichment, these mixture may also comprise significant amounts of sterols, fatty acids, triglycerides and other substances.

Suitable phospholipids are also those which are suitable for administration by inhalation on account of their physiological properties. These comprise, in particular, phospholipid mixtures which are extracted in the form of lecithin from natural sources such as soy beans or chickens egg yoke, preferably in hydrogenated form and/or freed from lysolecithins, as well as purified, enriched or partially synthetically prepared phospholipids, preferably with saturated fatty acid esters. Particularly preferred are purified, enriched or partially synthetically prepared medium- to long-chain zwitterionic phospholipids which are mainly free from unsaturation in the acyl chains and free from lysolecithins and peroxides. Of the phospholipid mixtures, lecithin is particularly preferred. Examples for enriched or pure compounds are dimyristoyl phosphatidyl choline (DMPC), distearoyl phosphatidyl choline (DSPC) and dipalmitoyl phosphatidyl choline (DPPC). Of these, DMPC is currently more preferred. Alternatively, phospholipids with oleyl residues and phosphatidyl glycerol without choline residue are suitable for some embodiments and applications of the invention.

Other ionic surfactants which may serve as solubility-enhancing agents are, for example, sodium lauryl sulfate, sodium cetylstearyl sulfate, sodium (or calcium or potassium) docusate, medium and long chain fatty acids, etc.

Other solubility-enhancing agents may be selected from various chemical groups, such as co-solvents, chaotropic salts, urea, and complexing agents, such as divalent cations. Particularly preferred among these are complexing agents, especially compounds from the class of pharmaceutically acceptable cyclodextrins.

Cyclodextrins (CDs) are cyclic oligosaccharides composed of (α-1,4)-linked α-D-glucopyranose units. They comprise a relatively hydrophobic central cavity and a hydrophilic external region. Because the monomeric units cannot rotate freely at the α-1,4-linkages, the shape of the molecules is more conical than cylindrical, with the primary hydroxyl groups located at the smaller part and the secondary hydroxyl groups at the larger part of the corms.

The most common cyclodextrins are α-, β-, and γ-cyclodextrins with 6, 7, and 8 glucopyranose units, respectively.

The diameter of the cavities are approximately 4.7 to 5.3 Å for α-cyclodextrins, 6.0 to 6.5 for β-cyclodextrins, and 7.5 to 8.3 for γ-cyclodextrins. The non-derivatised cyclodextrins exhibit aqueous solubilities of about 145 mg/ml (α-cyclodextrin), 18.5 mg/ml (β-cyclodextrin), and 232 mg/ml (γ-cyclodextrin) at 25° C.

Cyclodextrins are known for their capability of forming inclusion complexes with smaller molecules. If the host molecules themselves are poorly water-soluble, they may become solubilised in the form of such cyclodextrin inclusion complexes. Several pharmaceutical agents have been successfully formulated into marketed drug products which incorporate cyclodextrins as solubility-enhancing agents.

Examples of potentially useful cyclodextrins include the non-derivatised cyclodextrins, but also derivatives whose hydroxyl groups are alkylated or hydroxyalkylated, such as 2-hydroxypropyl-β-cyclodextrin, 2-hydroxypropyl-γ-cyclodextrin, esterified, such as maltosyl-β-cyclodextrin, and methyl-γ-cyclodextrin or etherified, such as the beta and gamma sulfoalkyl ether cyclodextrins (SAE-CD) such as sulfobutyl-β-cyclodextrin, sulfobutyl-γ-cyclodextrin. Particularly preferred at present are 2-hydroxypropyl-β-cyclodextrin, the SAE-CDs α-cyclodextrin, β-cyclodextrin, and γ-cyclodextrin. Particularly useful are the less toxic beta and gamma sulfoalkyl ether cyclodextrins (SAE-CD) where the chain lengths of their substituents may vary from 2-12 C atoms with respect to the alkyl and ether substituent, each. Among the latter, the configurations with 7 alkyl substituents per cyclodextrin molecule being etherified are most preferred including sulfobutyl-β-cyclodextrin (Captisol), and sulfobutyl-γ-cyclodextrin.

According to another embodiment, the poorly soluble active compound is enhanced in solubility by the presence of at least two solubility-enhancing excipients, such as a cyclodextrin and a surfactant, or a non-ionic and an ionic surfactant, a surfactant and an acid or base, or a cyclodextrin and an acid or base. Of course, more than two solubility-enhancing agents may also be combined and incorporated in the liquid formulation from which the aerosol is obtained, if such number of excipients is needed and appears pharmaceutically acceptable.

In another embodiment, divalent cations, particularly calcium and magnesium salts, such as calcium and/or magnesium chloride, or organic salts such as magnesium aspartate and gluconate may be used to improve both the solubility and the taste of aqueous formulations prepared from drugs belonging to the class of fluoroquinolones and macrolides. In addition, these salts can improve the solubility and stability of aqueous formulations when suitable pH values are selected. In case of insufficient storage stability, addition of sugars, such as lactose, sucrose, trehalose and/or sugar alcohols, such as xylitol, mannitol, isomaltol may be advantageous to prepare lyophilisates. Depending on the physical and chemical stability of the liquid composition, a commercially useful shelf life may not be achievable. For example, if the active compound is hydrolytically labile, it is possible that an aqueous liquid formulation with a shelf life of at least two years cannot be successfully formulated. As a further example, physical complex carrier systems, such as surfactant-stabilised nanoparticulate systems or colloidal drug carriers like liposomes may not be physically stable over a sufficient period of time to ensure the required shelf life.

In any of these cases, it may be useful to develop a solid-state formulation which can be reconstituted into a liquid composition prior to administration. The solid formulation comprises at least the active compound or, if the liquid phase of the aerosol is to comprise more than one active compound, the solid formulation comprises at least one of the active compounds.

Thus, in one embodiment of the invention the step of providing the liquid composition comprising the active compound comprises: (a) providing a solid composition comprising said active compound, (b) providing a liquid for reconstituting said solid composition, and (c) reconstituting said solid composition with said liquid to obtain a liquid composition comprising the active compound.

Depending on the design and composition of the aerosol's dispersed liquid phase, the solid composition for reconstitution may comprise further ingredients which may or may not be selected from any of the solid excipients disclosed herein-above. Among the preferred excipients are osmotic agents, such as inorganic salts; excipients for adjusting or buffering the pH, such as organic or inorganic salts, acids, and bases; bulking agents and lyophilisation aids, such as sucrose, lactose, mannitol, sorbitol, xylitol, and other sugar alcohols; stabilisers and antioxidants, such as vitamin E or vitamin E derivatives, ascorbic acid, sulphites, hydrogen sulphites, gallic acid esters, butyl hydroxyanisole, and butyl hydroxytoluene; ionic and nonionic surfactants, including phospholipids, such as those surfactants disclosed above; complexing agents, such as cyclodextrins, in particular those cyclodextrins that are disclosed above; furthermore taste-masking agents, disintegrants, colouring agents, sweeteners, and flavours.

The solid composition for reconstitution may be part of a pharmaceutical kit. Such kit preferably comprises the solid composition in sterile form.

The solid composition may be prepared by providing a liquid composition which is similar to the liquid composition to be aerosolised, and subsequently drying it, such as by lyophilisation. Similar means that the liquid composition from which the solid composition is prepared by drying may not comprise all solid ingredients of the ready-to-use liquid composition, for example in the case that the liquid carrier for reconstitution is designed to comprise one or more of the excipients. Also, it is not necessary that the concentrations of the ingredients are identical for these two liquid compositions.

Alternatively, the solid composition for reconstitution may be prepared by providing the active ingredient and, optionally, at least one excipient, in powder form and subsequently mixing these to form a powder mixture.

The solid composition is preferably packaged in closed containers each of which holds the amount of the formulation which contains a unit dose of the active compound in a volume range from about 0.25 to 5 ml. Alternatively, but presently less preferred because of the risk of microbial contamination, a container holds a plurality of unit doses. Additionally, the kit may comprise a liquid carrier for reconstituting the solid composition and for preparing a liquid composition for aerosolisation, wherein the aerosol is used for delivering the active compound(s) to the mucosa of the nose, the osteomeatal complex or one or more paranasal sinuses.

According to one embodiment, such liquid carrier may consist of water only. In other embodiments, the carrier also comprises one or more physiologically inactive ingredients, such as one or more excipients selected from buffers and pH-adjusting agents, salts, surfactants etc. The liquid carrier may be provided in separate packaging containers holding the amount of liquid which is needed for reconstituting an amount of solid formulation containing one unit dose. If the solid formulation is packaged in containers holding more than a unit dose, the liquid carrier may also packaged in larger containers. In this case, either the liquid carrier or the solid composition should also comprise a preservative, or a combination of preservatives, to prevent microbial growth after reconstitution.

The containers comprising the liquid carrier and the solid composition for reconstitution may comprise means for connecting them to each other in order to facilitate the combination of their respective contents and enable easy and convenient reconstitution. In one of the embodiments, the liquid carrier and the solid composition are filled in two separate chambers of a dual chamber device adapted to separately store the two components and to mix them on demand without having to withdraw them from the containers. In this way, reconstitution may be more convenient and can be conducted without microbial contamination.

Alternatively, the kit may comprise one or more means or devices which are adapted to withdraw the liquid carrier or to mix the two components conveniently and effectively. Preferably, the kit also contains printed instructions on how to reconstitute the formulation and on how the reconstituted liquid composition is to be aerosolised and administered in order to achieve the delivery of the active compound to the mucosa of the nasal cavity and/or of the paranasal sinuses.

In another embodiment the vial or container holding the dissolved drug can be inserted into the nebuliser device according to a kind of "luer lock principle" which will no longer require to open the vial first until the content can be dispensed into the medication holding cup of the nebuliser. Thus, the vial can be designed to act as the medication holding reservoir of a distinct nebuliser making sure that no mix up with other nebulisers will happen having not the novel aerosol delivery features. In another embodiment the vial or container may be designed such that it fits in a distinct holding setting which makes it possible, upon insertion, that the liquid can drain out and be nebulised by an aerosol generator.

The aerosol of the invention may be used for the prevention, management, or treatment of an affection, condition, symptom, or disease of, or related to, nasal structures or the mucosa of the nasal cavity and/or of the paranasal sinuses, for example acute and chronic sinusitis, such as allergic sinusitis, seasonal sinusitis, bacterial sinusitis, fungal sinusitis, viral sinusitis, frontal sinusitis, maxillary sinusitis, sphenoid sinusitis, ethmoid sinusitis, vacuum sinusitis; acute and chronic rhinitis, such as allergic rhinitis, seasonal rhinitis, bacterial rhinitis, fungal rhinitis, viral rhinitis, atrophic rhinitis, vasomotor rhinitis; any combination of rhinitis and sinusitis (i.e. rhinosinusitis); nasal polyps, nasal furuncles, epistaxis, wounds of the nasal or sinunasal mucosa, such as after injury or surgery; and dry nose syndrome. A particularly preferred use of the aerosol, and thus of the liquid composition from which the aerosol is obtained, is for the treatment of acute and chronic forms of sinusitis. Preferably, the use involves repeated administration, optionally according to a regular administration regimen over a period of at least three days, with at least one administration per day. According to another embodiment, the administration frequency is about twice or thrice a day. Optionally, the treatment involves a more frequent administration, such as 4 times a day or more often. If once daily administration is selected, it is also useful to select a time interval between two consecutive administrations in the range from about 18 to 30 hours, such as every evening, every noon, or every morning, in order to avoid long periods without medication.

Surprisingly it was found in a gamma-scintigraphy study using the apparatus according to the invention, that retention of the drug in the upper airways was 6 to 8 fold higher compared to published data from nasal sprays and nebulizers (Suman et al., Pharmaceutical Research, Vol. 16, No. 10, 1999), which indicates a sustained release effect, when a drug is delivered into paranasal cavities. This unexpected effect may allow a reduction of the dosing frequency compared to regimes as recommended for nasal sprays and other routes of nasal drug administration (C. Marriott et al., RDD Europe 2007, proceedings p. 179-185). Hence, the sinunasal drug delivery system according to the invention has the potential to improve patient's compliance, since dosing frequency may be reduced compared to current drug administration by nasal pump sprays, nasal drops or nebuliser treatments.

In a further aspect, the invention provides a method for producing a pharmaceutical aerosol for the delivery of an active compound to the mucosa of the nose, the osteomeatal complex or a paranasal sinus, said aerosol comprising a dispersed liquid phase and a continuous gas phase. The method comprises the steps of (a) providing an aerosol generator adapted for emitting an aerosol at an effective flow rate of less than about 5 liters per minute; (b) providing a means for effecting a pressure pulsation of an aerosol having a frequency in the range from about 10 to about 90 Hz; (c) providing a liquid composition comprising the active compound, wherein a unit dose of the active compound is comprised in a volume of less than about 5 ml of said liquid composition, and (d) simultaneously operating said aerosol generator for nebulising said liquid composition into an aerosol at an effective flow rate of less than about 5 liters/min and operating said means to effect a pressure pulsation of the aerosol at a frequency in the range from about 10 to about 90 Hz.

With regard to the optional features of this method, the optional features of the aerosol of the invention as described herein-above, as well as the features of the devices which have been described as suitable for producing such aerosol and the features of the liquid compositions which are useful for being nebulised in the context of the invention, should be applied to the present method mutatis mutandis.

In particular, the effective aerosol flow may be selected to be not more than about 4.5 liters per minute, or not more than about 3 liters per minute, or not more than about 2 liters per minute, or not more than about 1 liter per minute, respectively, such as about 0.5 or 0.3 liters per minute.

Again, it is believed that it is difficult to adapt certain types of aerosol generators to produce aerosols having an effective flow rate of less than about 5 liters/min, and in particular of not more than about 3 liters/min. While aerosol generators comprising jet nebulisers have in the past been adapted to emit a pulsating aerosol in combination with appropriate compressors which are capable of delivering pressurised air whose pressure fluctuates with a frequency of about 10 to about 90 Hz, these jet nebulisers typically require a substantial air or gas flow in order to convert a liquid into a nebulised aerosol.

Aerosols exhibiting the desirable effective flow rates may be produced by nebulisers which do not require a stream of air or gas for nebulising a liquid. For example, ultrasonic nebulisers and electronic vibrating membrane nebulisers are suitable devices for carrying out the invention.

The method involves the simultaneous operation of a suitable aerosol generator, converting a liquid into a nebulised aerosol, and of a suitable means for effecting the pressure pulsation of the aerosol. In the context of the present invention, simultaneous operation means that during one course of aerosol administration, both the aerosol generator and the pulsation means are operated to the effect that the aerosol emitted by the aerosol generator pulsates. Simultaneous operation may be achieved by operating both devices continuously and in a substantially synchronised manner over a defined period of time, such as over several minutes, in order to administer the aerosol; or it may be achieved, for example, by the intermittent operation of the aerosol generator and the pulsation means in short alternating cycles; or it may be achieved, for example, by the intermittent emission of the aerosol from the aerosol generator over a period of time during which the pulsation means is operated continuously. The essential item is that the aerosol which is emitted from the aerosol generator vibrates through the operation of the pulsation means.

As mentioned above, the means for effecting the pulsation of the aerosol may be integrated within the aerosol generator, in particular if the pressure fluctuations are to be superimposed on the main aerosol flow. Alternatively, the pulsation means can be an independent device, and the pressure fluctuations which it generates can be transmitted to the patient separately from the main aerosol flow, e.g. through a tube which is connected via a nosepiece to one of the nostrils, while the aerosol emitted from a nebuliser is introduced to the other nostril: also this setup leads to the same effect, i.e. the vibration of the aerosol.

In order to provide a convenient and effective method of administering the aerosol of the invention, an aerosol generator may be selected that is adapted for emitting a nebulised aerosol at a rate of at least about 0.1 ml of dispersed liquid phase per minute. According to another embodiment, the aerosol generator is adapted to emit, during continuous (non-intermittent) operation, at least about 0.15 ml of dispersed phase per minute, or at least about 0.175 ml per minute, at least about 0.2 ml/min, at least about 0.3 ml/min, such as about 0.3 to 0.5 ml/min. If an intermittent mode of operation is conducted, the average total output rate may be lower, depending on the relative duration of the intermittent "on" and "off" phases.

In a further aspect, the invention provides an apparatus for generating a pharmaceutical aerosol for the delivery of an active compound to the mucosa of the nose, the osteomeatal complex or a paranasal sinus. The apparatus comprises an aerosol generator adapted for emitting an aerosol at an effective flow rate of less than about 5 liters/min and a means for effecting a pressure pulsation of an aerosol having a frequency in the range from about 10 to about 90 Hz. As used herein, an apparatus is understood as one or more devices which work together for achieving the desired effect, in this case a vibrating aerosol having a low effective flow rate. Accordingly, it is not essential whether the components of the apparatus are constructed so that they are mechanically attached to each other or not. With regard to the optional features of the apparatus and its components, reference is made to the respective aspects of the description of the aerosol of the invention herein-above which also provides details on these features in various embodiments.

The invention makes it possible to use small volumes of liquid compositions of about 0.25 to 2.5 ml or even 0.5 to 1.5 ml for aerosol delivery to the paranasal cavities with a higher efficiency than described in the prior art.

The invention is further illustrated by the following examples which should not be understood as limiting the scope of the invention.

EXAMPLES

Example 1

An aqueous levofloxacin solution was nebulised by the inventive device generating a pulsating aerosol having a low effective flow rate. Its sinunasal deposition was evaluated in a human nasal cast in-vitro model.

Sinunasal Deposition Model

A human nasal cast model based on the anatomical shapes and dimensions of the nasal cavity and the nasal passage was built from plastic (polyoxymethylen). In this model, the paranasal sinuses are simulated by 6 exchangeable glass bottles, 3 on either side, representing the frontal, maxillary, and sphenoid sinuses, respectively. Exchangeable, artificial ostiae of 10 mm length were used to connect the artificial sinus cavities to the nose model. Moreover, the model has two openings representing artificial nostrils and one opening for the simulation of the pharynx which connects the nasal cavity with the trachea. The deposition model is also equipped with a pressure sensor inside the nasal cavity in order to determine the amplitude of the aerosol pressure pulsation.

The configuration used for this experiment included an internal volume of 7.5 ml for each of the frontal sinuses, 23 ml for each of the maxillary sinuses, and 13 ml for each of the sphenoid sinuses. The diameters of the ostiae were 1 mm (left side) and 3 mm (right side) for all sinuses. The interior space of each of the glass bottles representing the sinuses was lined with a patch of filter material.

Test Formulation

An aqueous liquid solution of levofloxacin comprising 3 wt.-% of the active ingredient was prepared. The inactive ingredients were xylitol (2 wt.-%), sodium chloride (0.029 wt.-%), magnesium sulphate heptahydrate (1.33 wt.-%), hydroxypropyl methylcellulose (0.01 wt.-%), and water.

Aerosol Generator and Pulsation Means

A prototype electronic vibrating mesh nebuliser was modified to receive an external air flow which transports the aerosol via a flexible tube and a tightly sealing nosepiece into one of the artificial nostrils of the cast model. An adapter nosepiece was fitted to the other nostril, the adapter comprising an outlet with a flow resistor and an inlet connecting it to a flexible tube connected with a vibration generator providing pressure pulsations of about 20 mbar (measured in the model) at a frequency of 36 Hz, but without any net air flow. In this particular setup, the flow transporting the aerosol to the model was substantially the same as the effective aerosol flow as defined above, since no additional net flow was added through the vibration generator and no significant loss or attenuation occurred.

Test Procedure

For each test, the nebuliser reservoir was charged with 0.5 ml of the levofloxacin solution. The nebuliser was then operated in a continuous mode with a defined aerosol flow until the reservoir was empty and the device automatically switched off. Simultaneously with the nebuliser, the vibration generator was operated in a continuous mode. Subsequently, the reservoir was again charged with 0.5 ml of the levofloxacin solution. The tube for transporting the aerosol to the cast model was now fitted to the other nostril, and the nebuliser and vibration generator were again operated simultaneously until the reservoir was empty. To evaluate the deposition of the aerosol, the model was then disassembled. The respective components were rinsed with a suitable solvent to extract the active ingredient, which was quantified by HPLC. Similarly, the drug content of the contacting areas of the nebuliser, of the remaining parts of the cast model, and of the filter inside the flow restrictor was analysed. The drug substance found in the remaining parts of the cast model was added to that found in the sinuses to estimate the total sinunasal deposition. Two complete test cycles were conducted for each flow rate.

Results

Table 1 shows the sinus deposition and total sinunasal deposition of levofloxacin for the various flow rates (in wt.-%). It is noted that the effective flow rates of 0.8, 1.5, 3.0, and 4.5 liters/min exhibit extraordinarily high degrees of sinus and sinunasal deposition, which are by far above any other deposition values found by the inventors when testing prior art methods and devices suggested for aerosol delivery to the sinuses or to the sinunasal mucosae. The nebulisation time for 2×0.5 ml was in the range of 3 to 3.5 minutes in all tests.

TABLE 1

| Flow rate (l/min) | Run | Sinus deposition | Total model (sinunasal) deposition | Total recovery |
|---|---|---|---|---|
| 0.8 | 1 | 19.9% | 62.2% | 96.4% |
| 0.8 | 2 | 22.0% | 67.2% | 95.8% |
| 1.5 | 1 | 22.2% | 64.6% | 84.6% |
| 1.5 | 2 | 22.0% | 61.0% | 85.9% |
| 3.0 | 1 | 19.5% | 52.2% | 95.9% |
| 3.0 | 2 | 19.7% | 54.1% | 93.9% |
| 4.5 | 1 | 16.5% | 44.9% | 86.2% |
| 4.5 | 2 | 16.6% | 45.0% | 87.0% |
| 7.0 | 1 | 9.3% | 28.1% | 96.1% |
| 7.0 | 2 | 10.4% | 28.8% | 94.8% |

Example 2

A comparative study of the apparatus of the invention as described in example 1, operated at a flow rate of 2 l/min (in this case this is also the effective flow rate), versus a PARI SINUS™ device which also emits a vibrating aerosol, equipped with the improved LC SPRINT Junior™ jet nebuliser with an effective flow rate of 7 l/min using the deposition model as described in example 1 was carried out. Both devices were adapted to produce aerosols with a mean droplet size of approximately 3 μm, the pressure amplitude of the vibration (measured in the model) was 20 mbar and the frequency was set at 44 Hz for both devices.

Test Formulation 15 mg levofloxacin dissolved in 3 ml isotonic saline. The low flow nebuliser was filled with 2×1.5 ml.

Results

As shown in Table 2 below, much higher drug deposition can be achieved with the low flow prototype apparatus compared to the PARI SINUS™ device with the same charged drug amount. Moreover, the administration time with the apparatus of the invention was significantly shorter than the administration time with the PARI SINUS™ device (6.7 min vs. 8.0 min).

TABLE 2

| Sinus Position and Dimensions | | | Deposited Drug in sinus [μg], depending on device type | |
|---|---|---|---|---|
| Position | Sinus volume [ml] | Ostium diameter [mm] | PARI SINUS ™ | Apparatus of invention |
| Frontal right | 7.5 | 3 | 24 | 188 |
| Frontal left | 7.5 | 1 | 71 | 251 |
| Maxillary right | 23 | 3 | 145 | 825 |
| Maxillary left | 23 | 1 | 86 | 284 |
| Sphenoid right | 12 | 3 | 53 | 401 |
| Sphenoid left | 12 | 1 | 74 | 360 |

Example 3

Test Formulation

An azithromycin formulation consisting of 5.0 wt.-% azithromycin, 2.0 wt.-% magnesium chloride hexahydrate, 0.0125 wt.-% menthol, 0.025 wt.-% sodium saccharine and 2.5 wt.-% xylitol and hydrochloric acid for pH adjustment to 6.3 was used to investigate the nebulization efficiency of the apparatus according to the invention. Due to the antimicrobial, anti-inflammatory and immunomodulatory effect of azithromycin this formulation will be particularly useful for the treatment of nasal and paranasal inflammations and infections. Furthermore, this drug formulation will also be suitable to treat nasal polyps when delivered with the apparatus according to the invention.

Test Procedure

First, the test formulation was nebulized with various aerosol generators (atomizing heads) and the mass median diameter was measured by laser diffraction. The head producing an aerosol with a mass median diameter of 3.0 μm was selected for the deposition study as described in Example 1. The device was operated with a constant flow rate of 1.0 l/min and a pulsation frequency of 36 Hz.

For each test, the nebuliser reservoir was charged with 0.5 ml of the azithromycin solution (50 mg/ml) as described above. The nebuliser was then operated in a continuous mode with a defined aerosol flow until the reservoir was empty and the device automatically switched off. Simultaneously with the nebuliser, the vibration means was operated in a continuous mode. Subsequently, the reservoir was again charged with 0.5 ml of the azithromycin solution. The tube for transporting the aerosol to the cast model was now fitted to the other nostril, and the nebuliser and vibration means were again operated simultaneously until the reservoir was empty. To evaluate the deposition of the aerosol, the model was then disassembled. The respective components were rinsed with a suitable solvent to extract the active ingredient, which was quantified by HPLC. Similarly, the drug content of the contacting areas of the nebuliser, of the remaining parts of the cast model, and of the filter inside the flow restrictor was analysed. The drug substance found in the remaining parts of the cast model was added to that found in the sinuses to estimate the total sinunasal deposition. The experiment was carried out four times Results. Table 3 shows the sinus deposition of azithromycin (in μg). 30% of the charged drug amount deposited in all six sinus cavities and 32% deposited in the nasal cavity. Consequently, the sinunasal deposition was 62%. The nebulisation time for 2×0.5 ml was in the range of 3.2 to 3.4 minutes in all tests.

TABLE 3

| Sinus Position and Dimensions | | | |
|---|---|---|---|
| Position | Sinus volume [ml] | Ostium diameter [mm] | Deposited Azithromycin in sinus [μg] |
| Frontal right | 7.5 | 0.5 | 214 |
| Frontal left | 7.5 | 0.5 | 312 |
| Maxillary right | 23 | 2 | 5039 |
| Maxillary left | 23 | 2 | 5568 |
| Sphenoid right | 12 | 1 | 1661 |
| Sphenoid left | 12 | 1 | 1908 |

Example 4

An aqueous budesonide formulation composed of the ingredients listed in Table 4 was used to investigate the nebulization efficiency of the apparatus according to the invention. First, the test formulation was nebulized with various aerosol generators (atomizing heads) and the mass median diameter was measured by laser diffraction. The head producing an aerosol with a mass median diameter of 3.0 µm was selected for the deposition study as described in Example 1. The device was operated with a constant flow rate of 1.0 µmin and a pulsation frequency of 36 Hz.

TABLE 4

Composition of test formulation

| Ingredient | [wt.-%] |
|---|---|
| Budesonide (Dose: 120 µg/0.5 ml) | 0.0236 |
| Captisol ™ | 3.57 |
| Citric acid, anhydrous | 0.03 |
| Sodium citrate, dihydrate | 0.05 |
| Sodium chloride | 0.57 |
| Disodium edetate, dihydrate | 0.01 |
| Water for injection | ad 100.0 |

Test Procedure

For each test, the nebuliser reservoir was charged with 0.5 ml of the budesonide solution. The nebuliser was then operated in a continuous mode with a defined aerosol flow until the reservoir was empty and the device automatically switched off. Simultaneously with the nebuliser, the vibration means was operated in a continuous mode. Subsequently, the reservoir was again charged with 0.5 ml of the budesonide solution. The tube for transporting the aerosol to the cast model was now fitted to the other nostril, and the nebuliser and vibration means were again operated simultaneously until the reservoir was empty. To evaluate the deposition of the aerosol, the model was then disassembled. The respective components were rinsed with a suitable solvent to extract the active ingredient, which was quantified by HPLC. Similarly, the drug content of the contacting areas of the nebuliser, of the remaining parts of the cast model, and of the filter inside the flow restrictor was analysed. The drug substance found in the remaining parts of the cast model was added to that found in the sinuses to estimate the total sinunasal deposition. The experiment was carried out three times Results Table 5 shows the sinus deposition of Budesonide (in µg). 28% of the charged drug amount deposited in all six sinus cavities and 33% deposited in the nasal cavity. Consequently, the sinunasal deposition was 61% of the initially charged drug mass. The nebulisation time for 2×0.5 ml was in the range of 3.3 to 3.5 minutes in all tests.

TABLE 5

Sinus Position and Dimensions

| Position | Sinus volume [ml] | Ostium diameter [mm] | Deposited Budesonide in sinus cavity[µg] |
|---|---|---|---|
| Frontal right | 7.5 | 0.5 | 0.5 |
| Frontal left | 7.5 | 0.5 | 0.5 |
| Maxillary right | 23 | 2 | 25.2 |
| Maxillary left | 23 | 2 | 28.0 |
| Sphenoid right | 12 | 1 | 8.3 |
| Sphenoid left | 12 | 1 | 9.5 |

Example 5

A scintygraphy study with $^{99m}$Tc-DTPA radiolabeled disodium cromoglycate solution (IsoCrom™ PARI Pharma, Munich, Germany) was carried out in two healthy volunteers as follows.

Test Procedure

The nebuliser reservoir was charged with approx. 1.0 ml of the $^{99m}$Tc-DTPA (diethylene triamine pentaacetic acid) labelled isotonic cromoglycate solution. The nebuliser was then operated in a continuous mode with a defined aerosol flow of 1.0 l/min and a pulsation frequency of 36 Hz for 10 seconds in each nostril. Immediately after administration, each volunteer was positioned in anterior position to the gamma camera to acquire deposition images. Additional images were obtained after different time periods up to 24 hours after the administration. The decay corrected counts of each image were plotted versus time and an exponential regression curve was fitted to the data. Half times ($T_{1/2}$) and time constants ($\tau$) were calculated from the regression equation. The data are shown in Table 6.

Published clearance data (Suman et al., "Comparison of nasal deposition and clearance of aerosol generated by a nebulizer and an aqueous spray pump", Pharmaceutical Research, Vol. 16, No. 10, 1999) were processed in the same way to obtain half time and time constant of activity retention of nasal sprays ($T_{1/2}$=0.75 h, $\tau$=1.0 h) and nebulizers ($T_{1/2}$=1.0 h, $\tau$=1.5 h).

TABLE 6

| Subject 1 | | Subject 2 | |
|---|---|---|---|
| Time [h] | Retention [%] | Time [h] | Retention [%] |
| 0.03 | 100 | 0.06 | 100 |
| 1.28 | 72.2 | 0.68 | 68.8 |
| 3.08 | 63.7 | 1.2 | 62.6 |
| 22.7 | 8.4 | 4.5 | 48.9 |
| | | 5.9 | 42.0 |
| | | 24.6 | 8.7 |
| Result: | $T_{1/2}$ = 6.3 h, $\tau$ = 9.1 h | | $T_{1/2}$ = 6.8 h, $\tau$ = 9.8 h |

The drug retention obtained upon drug administration via the apparatus according to the invention is about six fold higher compared to a nebulizers (about 6.5 h vs. 1 h) fitted for nasal drug administration and about eight fold higher than established metering nasal pump sprays (about 6.5 h vs. 0.75 h).

Example 6

Formulations for combination products consisting of two synergistically acting antibiotics to treat bacterial infections of the nose and paranasal cavities caused by chronic rhinosinusitis and/or cystic fibrosis can be composed of a macrolide with an aminoglycoside, a fluoroquinolone or a cefalosporine or a monobactam. Some examples making use of divalent ions as complex forming excipients are given below.

Example 6-1

A combination product of azithromycin monohydrate ethanolate with tobramycin was formulated as follows: 5.0 g of azithromycin was dissolved in about 82 g of water for injection employing HCl (1 M). An equimolar amount of magnesium chloride hexahydrate (about 1.4 g) was added to the solution and stirred until completely dissolved. The other taste masking agents trehalose (2.0 wt.-%), saccharin sodium (0.025 wt.-%) and L-menthol (0.025 wt.-%) were added and dissolved under stirring, then the pH was adjusted to pH 6.3 with 1 N NaOH and the volume made up to 100 ml. Then, 10.0 g of tobramycin was added to this solution. The final solution was sterile filtered under laminar air flow and 0.5 ml thereof was filled into a polyethylene blow fill seal vial which was sealed thereafter. The osmolarity of this formulation was measured to be 748 mOsmol/kg after being stored at 2-8° C. for three weeks.

Example 6-2

5.0 g of azithromycin monohydrate ethanolate and about 2.5 g magnesium chloride hexahydrate were dissolved in about 86 g of water for injection by adding dropwise 1 N HCl to reach a pH of about 6. 3.0 g of levofloxacin was added and the mixture was stirred until dissolved. Thereafter the pH was adjusted to pH 6.3 with NaOH and the volume adjusted to 100 ml. The resulting clear solution was sterile filtered under laminar air flow. Then, 2 ml of the solution was filled into pre-sterilized nitrogen gassed polypropylene blow fill seal vials.

Example 7

This example describes the manufacture of a lyophilisate comprising of 75 mg/ml aztreonam and 75 mg/ml azithromycin as a combination product for nebulization via the apparatus according to the invention to treat infections of the nose and paranasal cavities caused by gram negative and gram positive bacteria.

About 7.5 g of aztreonam was suspended in about 75 ml of water for injection. 90% of the calculated amount of lysine-monohydrate was dissolved in about 15% of the calculated amount of water for injection (neutralizing solution I). The lysine-monohydrate solution (neutralizing solution I) was slowly added to the aztreonam suspension under constant stirring and pH-control (pH-meter). 5.0 g of lysine-monohydrate was dissolved in 50.0 ml of water for injection (neutralizing solution II). This solution (neutralizing solution II) was added to the neutralized aztreonam solution until the desired pH-value is obtained (under constant stirring and pH-control). Water for injection was added to obtain the calculated final volume (=lyophilization solution). To this aztreonam solution was added an azithromycin solution (75 mg/ml) prepared as follows:

7.6 g of azithromycin monohydrate ethanolate was dissolved in about 90 g water for injection employing HCl (1 M). 3% mannitol and about 2.1 g magnesium chloride hexahydrate was added to the solution and stirred until completely dissolved. The pH was adjusted to pH 6.3 with 1 N NaOH and the volume was made up to 100 ml by addition of water for injection.

Thereafter, about 90 ml of both solutions were mixed together in a ratio of 1:1 and filtered through 0.22 µm filter. 4 ml aliquots were filled in pre-sterilized amber glass vials and placed in the freeze dryer (Christ Epsilon 2-6D) and lyophilized according to the conditions as stated below.

Freezing: 6 hours, −40° C., no vacuum
Primary drying: 18 hours, −10° C., 0.25 mbar
Secondary drying: 18 hours, +20° C., 0.04 mbar After completion of the drying cycles the vials were closed within the freeze-dryer and sealed thereafter. The cake was dissolved in 2 ml sterile water and the solution was delivered as aerosol with the novel paranasal drug delivery system to treat a patient suffering from an infection caused by gram negative and gram positive bacteria and which has failed effective treatment with various classes of intravenous and oral antibiotics.

The invention claimed is:

1. A method for producing a pharmaceutical aerosol for the delivery of an active compound to the mucosa of the nose, the osteomeatal complex or a paranasal sinus, said aerosol comprising a dispersed liquid phase and a continuous gas phase, said method comprising:
   (a) providing an aerosol generator adapted for emitting an aerosol at an effective flow rate of less than 5 liters/min of the gas phase;
   (b) providing a means for effecting a pressure pulsation of an aerosol having a frequency in the range from 10 to 90 Hz;
   (c) providing a liquid composition comprising said active compound, wherein a unit dose of the active compound is comprised in a volume of less than 5 ml of said liquid composition, and
   (d) operating said aerosol generator for nebulising said liquid composition into an aerosol at an effective flow rate of less than 5 liters/min of the gas phase and operating said means to effect a pressure pulsation of the aerosol at a frequency in the range from 10 to 90 Hz in such a way that a non-constant effective aerosol flow is achieved which includes one or more phases of absent effective aerosol flow wherein the duration of the phases of absent effective aerosol flow is in the range from 1 millisecond to 10 seconds;
   wherein the effective flow rate is the flow rate of the aerosol as it enters the respiratory system of the patient.

2. The method of claim 1, wherein the aerosol generator emits the aerosol at an effective flow rate of not more than 3 liters/min of the gas phase.

3. The method of claim 1, wherein the means for effecting a pressure pulsation maintains an amplitude of pressure pulsation of at least 5 mbar.

4. The method of claim 1, wherein the aerosol generator emits the aerosol at a density of at least 0.05 µl of dispersed liquid phase per ml of continuous gas phase.

5. The method of claim 1, wherein the aerosol generator includes a nebuliser selected from the group consisting of ultrasonic nebulisers and electronic vibrating membrane nebulisers.

6. The method of claim 1, wherein a unit dose of the active compound is comprised in a volume of less than 2.5 ml of the liquid composition.

7. The method of claim 1, wherein the aerosol generator emits a quantity of aerosol comprising a unit dose of the active compound within less than 10 minutes.

8. The method of claim 1, wherein the mass median diameter of the dispersed liquid phase is from 2.0 to 6.0 µm, as measured by laser diffraction.

9. The method of claim 1, wherein the aerosol is emitted at a first effective flow rate which is larger than zero for a first time period, followed by a second time period during which the aerosol is emitted at a second flow rate, which is zero.

10. The method of claim 9, wherein the first time period has a duration which ensures that the sinunasal region is filled with a new portion of the aerosol.

11. The method of claim 9, wherein the duration of the second time period is from 0.5 to 2 seconds.

12. The method of claim 1, wherein the aerosol is emitted during alternating phases (i) of absent effective aerosol flow during which the pressure of the aerosol pulsates and (ii) of an effective aerosol flow which is different from zero during which the aerosol does not pulsate.

13. The method of claim 1, wherein the step of providing the liquid composition comprising the active compound comprises: (a) providing a solid composition comprising said active compound,
(b) providing a liquid for reconstituting said solid composition, and
(c) reconstituting said solid composition with said liquid to obtain a liquid composition comprising the active compound.

14. The method of claim 1, wherein the active compound is selected from the group consisting of: anti-inflammatory compounds, anti-allergics, antibiotics, antibodies, antifungals, anti-infective agents, antioxidants, antiseptics, antivirals, cytostatics, decongestants, genes, glucocorticoids, immunomodulators, leucotriene antagonists, local anesthetics, mucolytics, oligonucleotides, peptides, plant extracts, proteins, vaccines, vitamins, and wound healing agents.

15. The method of claim 1, wherein the active compound comprises a macrolide in a concentration of 10 to 100 mg/ml and the liquid composition comprises divalent cations and wherein the ratio of the total molar concentration of divalent cations to the molar concentration of the macrolide is in the range of from 0.1:1 to 10:1.

16. The method of claim 15, wherein the macrolide is azithromycin.

17. The method of claim 15, wherein the divalent cations are selected from water soluble inorganic and organic salts of calcium and magnesium.

18. The method of claim 1, wherein the active compound is a combination of azithromycin and a fluoroquinolone or an aminoglycoside in a ratio in the range from 1:3 to 3:1.

19. A pharmaceutical aerosol for the delivery of an active compound to the mucosa of the nose, the osteomeatal complex or a paranasal sinus, generated from a liquid composition comprising a unit dose of an active compound in a volume of less than 5 ml of said liquid composition, said aerosol comprising a dispersed liquid phase and a continuous gas phase, wherein the pressure of said aerosol pulsates with a frequency in the range from 10 to 90 Hz, wherein said aerosol exhibits an effective flow rate of less than 5 liters/min of the gas phase, wherein the effective aerosol flow is a non-constant effective aerosol flow which includes one or more phases of absent effective aerosol flow wherein the duration of the phases of absent effective aerosol flow is in the range from 1 millisecond to 10 seconds, and wherein the effective flow rate is the flow rate of the aerosol as it enters the respiratory system of the patient.

20. The aerosol of claim 19, wherein the effective flow rate is not more than 3 liters/min of the gas phase.

21. The aerosol of claim 19, wherein the pressure pulsates with an amplitude of at least 5 mbar.

22. The aerosol of claim 19, having a density of at least 0.05 µl of dispersed liquid phase per ml of continuous gas phase.

23. The aerosol of claim 19, wherein the mass median diameter of the dispersed liquid phase is from 2.0 to 6.0 µm, as measured by laser diffraction.

24. The aerosol of claim 19, wherein the active compound is selected from the group consisting of: anti-inflammatory compounds, anti-allergics, antibiotics, antibodies, antifungals, anti-infective agents, antioxidants, antiseptics, antivirals, cytostatics, decongestants, genes, glucocorticoids, immunomodulators, leucotriene antagonists, local anesthetics, mucolytics, oligonucleotides, peptides, plant extracts, proteins, vaccines, vitamins, and wound healing agents.

25. The aerosol of claim 19, wherein the active compound comprises a macrolide in a concentration of 10 to 100 mg/ml and the liquid composition comprises divalent cations and wherein the ratio of the total molar concentration of divalent cations to the molar concentration of the macrolide is in the range of from 0.1:1 to 10:1.

26. The aerosol of claim 25, wherein the macrolide is azithromycin.

27. The aerosol of claim 25, wherein the divalent cations are selected from water soluble inorganic and organic salts of calcium and magnesium.

28. The aerosol of claim 19, wherein the active compound is a combination of azithromycin and a fluoroquinolone or an aminoglycoside in a ratio in the range from 1:3 to 3:1.

29. The method of claim 1, wherein the aerosol is delivered for the prevention, management, or treatment of asthma, cystic fibrosis, acute or chronic sinusitis or nasal polyps.

30. The method of claim 1, wherein the aerosol is administered at a frequency of at least once, twice or three times weekly, or once daily over a period of at least three days.

31. An apparatus for generating a pharmaceutical aerosol for the delivery of an active compound to the mucosa of the nose, the osteomeatal complex or a paranasal sinus, comprising an aerosol generator adapted for emitting an aerosol at an effective flow rate of less than 5 liters/min of the gas phase and a means for effecting a pressure pulsation of an aerosol having a frequency in the range from 10 to 90 Hz, wherein said aerosol generator and said means are configured in such a way that a liquid composition filled into the apparatus and comprising a unit dose of an active compound in a volume of less than 5 ml of said liquid composition can be nebulized into an aerosol at an effective flow rate of less than 5 liters/min of the gas phase and with a pressure pulsation having a frequency in the range from 10 to 90 Hz, and that a non-constant effective aerosol flow can be achieved which includes one or more phases of absent effective aerosol flow, wherein the duration of the phases of absent effective aerosol flow is in the range from 1 millisecond to 10 seconds, and wherein the effective flow rate is the flow rate of the aerosol as it enters the respiratory system of the patient.

32. The apparatus of claim 31, wherein the aerosol generator is adapted for emitting an aerosol at an effective flow rate of not more than 3 liters/min of the gas phase.

33. The apparatus of claim 31, wherein the means for effecting a pressure pulsation is adapted to maintain an amplitude of pressure pulsation of at least 5 mbar.

34. The apparatus of claim 31, wherein the aerosol generator includes a nebuliser selected from the group consisting of ultrasonic nebulisers and electronic vibrating membrane nebulisers.

35. The apparatus of claim 31, wherein the nebuliser comprises a first nosepiece through which the aerosol is emitted, and wherein the means for effecting a pressure pulsation comprises a second nosepiece through which the pressure pulsation is transmitted.

36. The apparatus of claim 31, wherein the nebuliser produces an aerosol which can be deposited to the paranasal cavities and has a different clearance mechanism and longer residence time compared to the aerosol depositing to the nose.

37. The apparatus of claim 31, characterized by an in-vitro paranasal drug deposition of at least 8% when applying a human nasal cast model and an in- vivo clearance rate of less than 50% in two hours of the nominal dose.

38. The use of the apparatus of claim 31 for the prevention, management, or treatment of any lower or upper respiratory tract disease, or of any symptom or condition caused by any lower or upper respiratory tract disease, wherein the use comprises the steps of (i) generating a pharmaceutical aerosol with the apparatus of claim 31 and (ii) administering the aerosol to the subject.

39. The use of claim 38, wherein the disease is asthma, cystic fibrosis, acute or chronic sinusitis or nasal polyps.

40. A method for the prevention, management, or treatment of any lower or upper respiratory tract disease or any symptom or condition caused by such a disease in a subject in need of such prevention, management, or treatment, wherein the method comprises the steps of (i) producing a pharmaceutical aerosol according to the method of any of claims 1 to 12 and (ii) administering the aerosol to the subject.

41. The method of claim 40, wherein the disease is asthma, cystic fibrosis, acute or chronic sinusitis or nasal polyps.

42. The method of claim 40, wherein the active compound comprises a macrolide in a concentration of 10 to 100 mg/ml and the liquid composition comprises divalent cations and wherein the ratio of the total molar concentration of divalent cations to the molar concentration of the macrolide is in the range of from 0.1:1 to 10:1.

43. The method of claim 42, wherein the macrolide is azithromycin.

44. The method of claim 42, wherein the divalent cations are selected from water soluble inorganic or organic salts of calcium and magnesium.

45. The method of claim 40, wherein the active compound is a combination of azithromycin and a fluoroquinolone or an aminoglycoside in a ratio in the range from 1:3 to 3:1.

* * * * *